(12) United States Patent
Ziessel et al.

(10) Patent No.: US 9,328,088 B2
(45) Date of Patent: May 3, 2016

(54) LUMINESCENT PROBES FOR BIOLOGICAL LABELING AND IMAGING, AND PROCESS FOR PREPARING THE SAME

(71) Applicant: CENTRE NATIONAL DE LA RECHERCHE SCIENTIFIQUE, Paris (FR)

(72) Inventors: Raymond Ziessel, Souffelweyersheim (FR); Mathieu Starck, Strasbourg (FR); Alexandra Sutter, Wittelsheim (FR)

(73) Assignee: CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 22 days.

(21) Appl. No.: 14/345,705

(22) PCT Filed: Sep. 20, 2012

(86) PCT No.: PCT/FR2012/052104
§ 371 (c)(1),
(2) Date: Mar. 19, 2014

(87) PCT Pub. No.: WO2013/041811
PCT Pub. Date: Mar. 28, 2013

(65) Prior Publication Data
US 2014/0213777 A1    Jul. 31, 2014

(30) Foreign Application Priority Data
Sep. 22, 2011 (FR) .......................... 11 58433

(51) Int. Cl.
| | | |
|---|---|---|
| *C07F 5/00* | (2006.01) |
| *C07D 401/04* | (2006.01) |
| *C07D 401/14* | (2006.01) |
| *C07F 9/6558* | (2006.01) |
| *C07D 497/04* | (2006.01) |
| *G01N 33/533* | (2006.01) |

(52) U.S. Cl.
CPC ............ *C07D 401/04* (2013.01); *C07D 401/14* (2013.01); *C07D 497/04* (2013.01); *C07F 9/65583* (2013.01); *G01N 33/533* (2013.01)

(58) Field of Classification Search
CPC .. C07D 401/04; C07D 401/14; C07D 497/04; C07F 9/65583; G01N 33/533
USPC .......................................................... 534/15
See application file for complete search history.

(56) References Cited

FOREIGN PATENT DOCUMENTS

FR    2935973    3/2010

OTHER PUBLICATIONS

Santos et al. Bioorg. Med. Chem. Lett. 2014, 14, 3473-3476.*
Kadjane et al. Inorg. Chem. 2009, 48, 4601-4603.*
Ziessel et al. Tetrahedron Lett. 2012, 53m 3713-3716.*
Ziessel et al. Dalton Trans. 2006, 3285-3290.*
Hinderberger al. Angew. Chem. Int. Ed. 2004, 43, 4616-4621.*
Katia et al. Inorg. Chem. 2011, 50, 1689-1697.*
Search Report Dated 2012.
"Towards Libraries of luminescent lanthanide complexes and labels from generic synthons" Starck et al. Dated Aug. 8, 2011.
"Charge transfer excited states sensitization of lanthanide emitting from the visible to the near-infra-red" D'Aleo et al. Dated Mar. 1, 2012.

* cited by examiner

*Primary Examiner* — Maria Leavitt
*Assistant Examiner* — Sean R Donohue
(74) *Attorney, Agent, or Firm* — Sofer & Haroun, LLP

(57) ABSTRACT

The present invention relates to organic compounds, usable as ligands in the preparation of lanthanide complexes or of certain water-soluble transition metals, a method for preparation thereof, and the use of said organic compounds as fluorescent probes.

11 Claims, No Drawings

LUMINESCENT PROBES FOR BIOLOGICAL LABELING AND IMAGING, AND PROCESS FOR PREPARING THE SAME

RELATED APPLICATIONS

This application is a National Phase Application of PCT/FR2012/052104, filed on Sep. 20, 2012, which in turn claims the benefit of priority from French Patent Application No. 11 58433 filed on Sep. 22, 2011, the entirety of which are incorporated herein by reference.

BACKGROUND

1. Field of the Invention

The present invention relates to organic compounds which may be used as ligands for the preparation of water-soluble complexes of lanthanides or of certain transition metals, to a process for preparing the same, and to the use thereof as fluorescent probes.

2. Description of Related Art

Lanthanide ion complexes have very particular spectroscopic properties that allow applications in the field of the detection by luminescence. These complexes have a very wide Stokes shift, very fine emission lines, of the order of a few nm, which are characteristic of the lanthanide ion used. They can emit in the visible or near infrared region, and have an extremely long half-life of the excited state, which may be up to a millisecond. This last feature is an essential asset; it allows time-resolved detection (which makes it possible to eliminate the parasite fluorescence signals) and brings about a very large increase in the detection sensitivity of the complexes by luminescence microscopy or in fluoroimmunological analyses. Luminescent lanthanide ion complexes consequently have applications in the majority of the fields of conventional fluorescence.

However, lanthanide ion complexes are generally difficult to obtain. Many properties of the complex are dependent on the structure of the ligand and of the lanthanide ion, especially the excitation efficacy of the complex, the degree of stability of the lanthanide complexation in competitive chemical medium and in serum medium (which must be high to prevent release of the cations), the quantum luminescence yield and the possibility of forming covalent bonds with the material to be labeled for the biological applications of the complexes. Adequate excitation of the complexes may be obtained when the ligand of the complex comprises heteroaromatic groups whose function is to capture light and transfer it to the lanthanide ion which will reemit. This phenomenon is known as the antenna effect. The choice of these heteroaromatic groups defines many spectroscopic properties of the final complex, especially the spectral excitation range and the quantum luminescence yield.

CN-1811429-A describes a complex of $Tb^{3+}$ and of a ligand which has a 2,6-dipyrazolypyridine backbone in which each of the pyrazolyl groups bears a —$CH_2$—$N(CH_2CO_2H)_2$ group. Said complex is useful for detecting singlet oxygen. It is obtained via a process which consists in attaching the anthracene group to a dibromo-aminopyridine, and then in modifying the pyridyl group by reacting the bromine atoms with suitable reagents to replace each Br with a pyrazolyl group bearing a —$CH_2$—$N(CH_2CO_2H)_2$ group.

EP-0 770 610 describes lanthanide ion complexes in which the ligand is a 2,6-dipyrazolypyridine backbone in which each of the pyrazolyl groups bears a —$CH_2$—$N(CH_2CO_2H)_2$ group. The preparation process consists in first preparing a dibromo 2,6-dipyrazolypyridine compound, which is then modified to obtain the two —$CH_2$—$N(CHG_2CO_2H)_2$ end groups. This process does not make it possible to obtain compounds in which the pyridyl group bears substituents chosen to adjust the properties of the lanthanide complex in which said compounds constitute the ligand.

FR-2 935 973 describes ligands derived from 2,6-dipyrazolypyridine in which each of the pyrazolyl group bears a —$CH_2$—$N(CHG_2CO_2R)_2$ group in which each of the R groups represents H or an alkali metal or a quaternary ammonium group, the pyrazolyl groups also possibly bearing one or two substituents chosen from an alkyl group containing from 1 to 4 carbon atoms, or alternatively these two substituents together form a diradical forming an aromatic ring with the two carbon atoms that bear them. These ligands are capable of complexing lanthanide ions and find applications in labeling and biphotonic microscopy. However, they have poor solubility in water and great instability in purely aqueous medium, in saline medium or in purely biological medium.

OBJECTS AND SUMMARY

The aim of the present invention is to provide compounds that are useful as ligands for lanthanide or transition metal complexes which have improved solubility in water and in biological media, and also excellent chemical stability, very good luminescence properties and very long half-lives.

This aim is achieved with the compounds that form the subject of the present invention and which will be described hereinbelow.

A compound according to the present invention corresponds to formula (I) below:

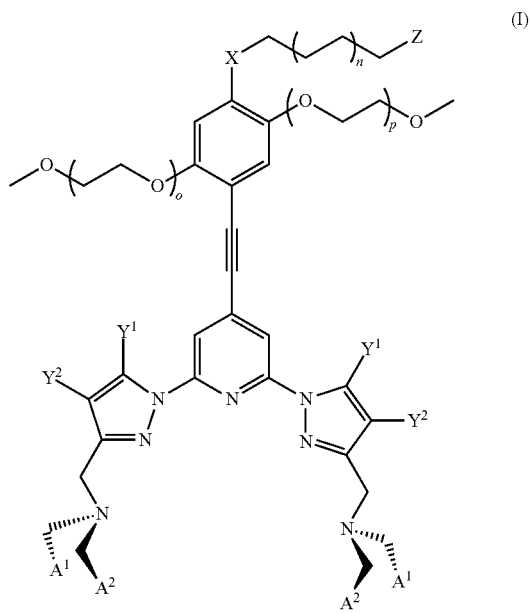

in which:
n, o and p, independently of each other, are integers ranging from 0 to 4;
$A^1$ represents a function —$COOR^1$ in which $R^1$ is a hydrogen atom or an alkali metal cation; or a group $A^2$;
$A^2$ represents a group —$P(O)(OCH_2CH_3)(OR^2)$ or —$P(O)(OR^2)_2$ in which $R^2$ represents a hydrogen atom or an alkali metal cation;

each of the groups $Y^1$ and $Y^2$ represents a hydrogen atom or alternatively $Y^1$ and $Y^2$ together form a diradical forming one or more aromatic or heteroaromatic rings with the two carbon atoms that bear them, said aromatic rings optionally bearing one or more substituents chosen from a hydrogen atom, an amino group and a thiol group, X represents a bond segment consisting of a group chosen from an amide function —C(O)—NH— and a triple bond —C≡C—;

Z is:
  $NH_2$, a halogen, a phosphate,
  a group $COOR^3$ in which $R^3$ is H, an alkali metal cation, a quaternary ammonium group $N(R^4)_4^+$ in which $R^4$ is H or a linear alkyl chain preferably containing from 1 to 4 carbon atoms, a succinimide group —N—(CO—$CH_2$—$CH_2$—CO)— or a pentafluorophenyl group —$C_6F_5$;
  a biotin function (—CO—$(CH_2)_4$—$C_5H_7N_2OS$), a polyheteroaromatic group or a crown ether,
  an organic or mineral silyl cluster;
  a macroscopic support, for instance a silica bead, a nanolatex bead or any other support that can be functionalized.

Among the alkali metal cations mentioned for $R^1$ and $R^2$, mention may be made in particular of $K^+$, $Na^+$ and $Li^+$.

The compounds of formula (I) in which the groups $Y^1$ and $Y^2$ form part of an aromatic or heteroaromatic ring are particularly preferred.

A compound of formula (I) according to the present invention may be prepared from a compound corresponding to one of the formulae (V) and (V') below:

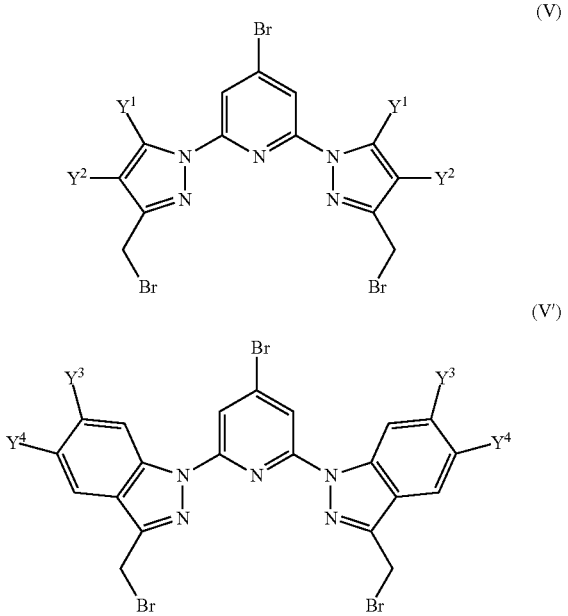

in which the groups $Y^1$ and $Y^2$ have the same meaning as that indicated above for the compounds of formula (I) and the groups $Y^3$ and $Y^4$, which may be identical or different, are chosen from a hydrogen atom, an amino group and a thiol group.

The compounds of formulae (V) and (V') may be prepared according to the process described in the patent application FR-2 935 973.

More precisely, and by way of example, the compounds of formula (I) may be prepared according to a process comprising the following steps:

i) a first step of nucleophilic substitution of the bromine atoms of a compound of formula (V) or (V'), in an anhydrous solvent such as anhydrous acetonitrile, in the presence of a mineral base chosen, for example, from $K_2CO_3$, $Na_2CO_3$ and $Cs_2CO_3$ and of a compound chosen from the compounds of formula (III) below [$NH(CH_2COOR'^1)(CH_2P(O)(OR'^2)_2)$] and the compounds of formula (IV) below [$NH\{CH_2P(O)(OR'^2)_2\}_2$] in which $R'^1$ and $R'^2$, independently of each other, represent a linear or branched $C_1$-$C_4$ alkyl radical, said nucleophilic substitution being performed at a temperature of between about 60° C. and 80° C. to obtain a compound of formula (VI) or, respectively, of formula (VI'), below:

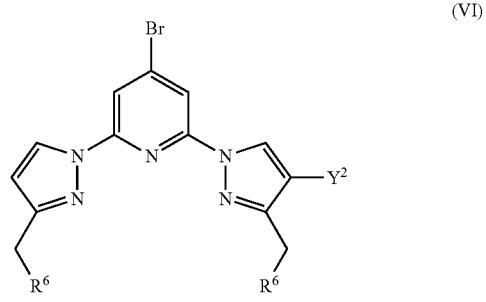

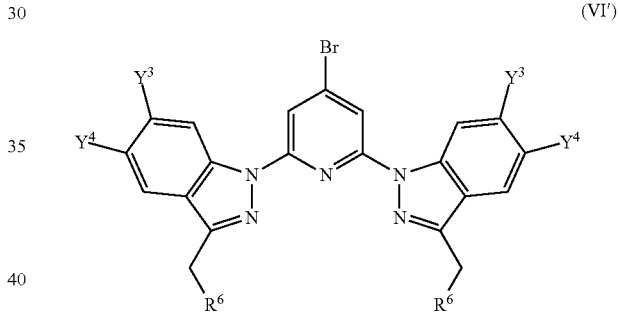

in which $R^6$ is chosen from the groups of formula $R^6$-a or $R^6$-b below:

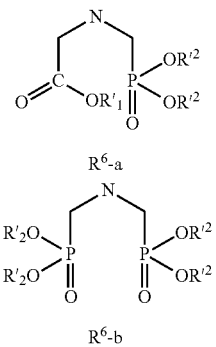

in which:
  $R'^1$ represents a linear or branched $C_1$-$C_4$ alkyl radical, for instance an ethyl or tert-butyl radical;
  $R'^2$ represents a $C_1$-$C_4$ radical, for instance an ethyl radical;
  ii) a second step of preparation of a compound 4 having the following formula:

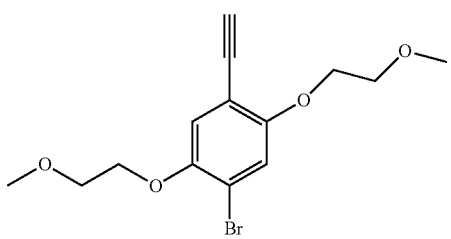

4 according to a process comprising the following substeps:

ii-a) the reaction of para-diphenol with 2-methoxyethanol tosylate, in an anhydrous solvent such as anhydrous acetonitrile in the presence of a mineral base chosen, for example, from $K_2CO_3$, $Na_2CO_3$ and $Cs_2CO_3$, at a temperature of about 80° C. for 12 hours approximately to obtain a compound 1 having the following formula:

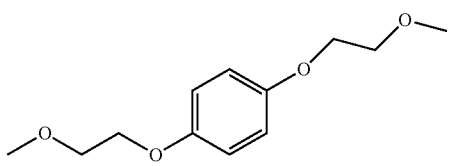

1 ii-b) a step of bromination of compound 1 obtained in the preceding step with bromine ($Br_2$), in a solvent such as refluxing tetrachloromethane for about 12 hours to obtain a compound 2 having the following formula:

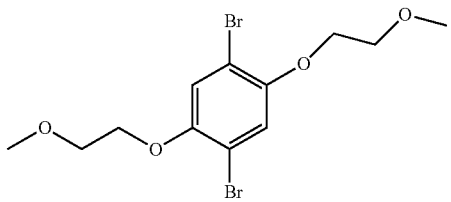

2 ii-c) a step of substitution of one of the two bromine atoms of compound 2 obtained in the preceding step, in a solvent such as tetrahydrofuran (THF), in the presence of diisopropylamine, a reagent $(CH_3)_2C(OH)C\equiv CH$ and a palladium catalyst such as a complex of palladium and of triphenylphosphine, in particular $Pd(PPh_3)_2Cl_2$, and CuI, to obtain a compound 3 having the following formula:

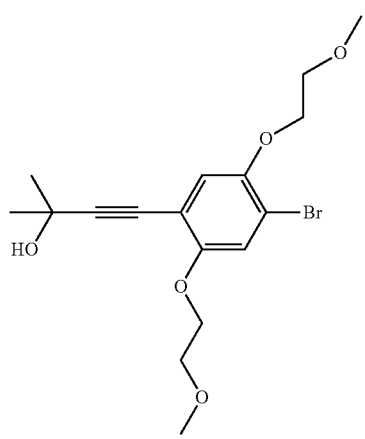

3 ii-d) a step of alkaline hydrolysis of compound 3 obtained above in the preceding step with an anhydrous strong base such as anhydrous NaOH, in an organic solvent such as toluene at a temperature of about 130° C. for 12 hours approximately, to obtain said compound 4;

iii) a third step of crossed coupling between compound 4 obtained above in step ii) and the compound of formula (VI) or, respectively, of formula (VI') obtained above in step i), in an organic solvent in the presence of a catalyst with palladium and triphenylphosphine, in particular $Pd(PPh_3)_2Cl_2$, to obtain a compound of formula (VII) or, respectively, (VII'), below:

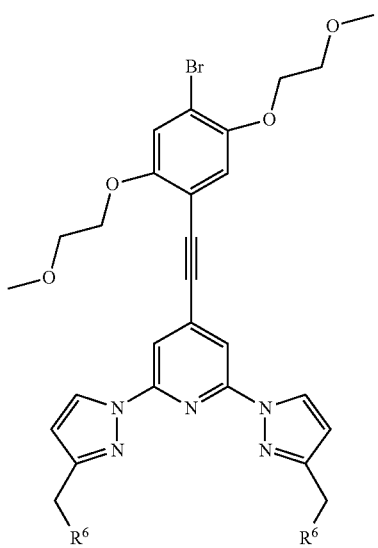

(VII)

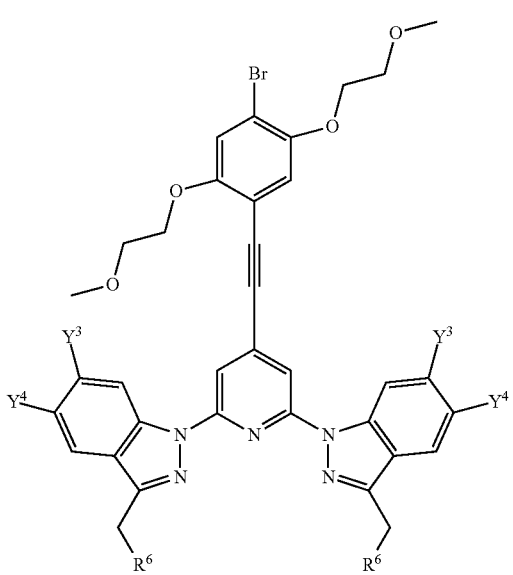

(VII')

in which $R^6$ has the same meaning as in the compounds of formula (VI) or, respectively, (VI'), above;

iv) a fourth step in which the bromine of the compound of formula (VII) or, respectively, (VII') is replaced with a group of formula X—CH$_2$—(CH$_2$CH$_2$)$_n$—CH$_2$—Z in which n, X and Z have the same meaning as that indicated above relating to the compounds of formula (I), by reaction with a suitable reagent, in the presence of an organometallic catalyst, in an organic solvent;

v) a fifth step in which the groups R'$^1$ and R'$^2$ are replaced, respectively, with groups R$^1$ and R$^2$, said groups being H or an alkali metal cation (for R$^1$) or an alkali metal cation (for R$^2$).

According to a preferred embodiment of the process for preparing the compounds of formula (I), step iv) of substitution of the bromine atom with the group of formula X—CH$_2$—(CH$_2$CH$_2$)$_6$—CH$_2$—Z is performed under crossed coupling conditions of Sonogashira type or of carboamidation type catalyzed with sub-liganded palladium.

In the fifth step, the replacement of the groups R'$^1$ and R'$^2$ of the linear alkyl type with a cation K$^+$, Na$^+$ or Li$^+$ may be performed with KOH, NaOH or LiOH, respectively, in a polar solvent (for example a CH$_3$OH/H$_2$O mixture), at a temperature of between 20 and 100° C., for example at 60° C., or alternatively by using trimethylsilyl bromide in a solvent such as dichloromethane at room temperature followed by basic hydrolysis. The group COOK, COONa or COOLi can then, if necessary, be modified to an acid group by reaction with an acid such as HCl in water.

Also during the fifth step, the replacement with H of groups R'$^1$ or R'$^2$ of the branched alkyl type may be performed by reaction with trifluoroacetic acid (TFA) in an aprotic organic solvent.

A few examples of ligands, to which the invention is, however, not limited, are given below for purely illustrative purposes. Similar ligands may be obtained by replacing Na with one of the other groups R$^1$ or R$^2$ as defined previously.

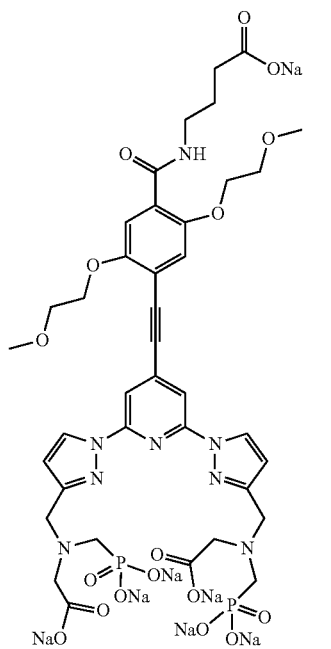

(I-1)

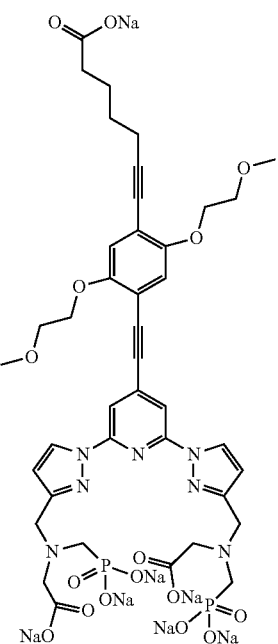

(I-2)

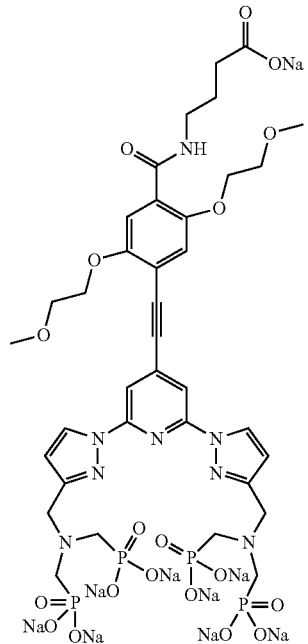

(I-3)

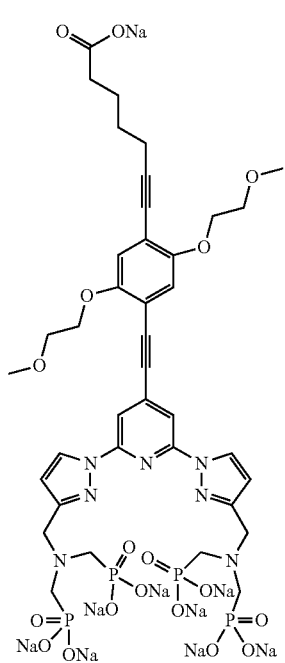
(I-4)
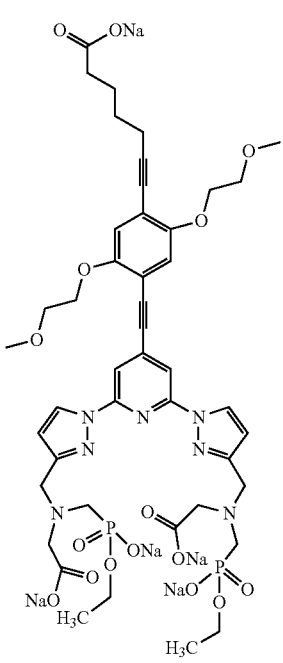
(I-6)
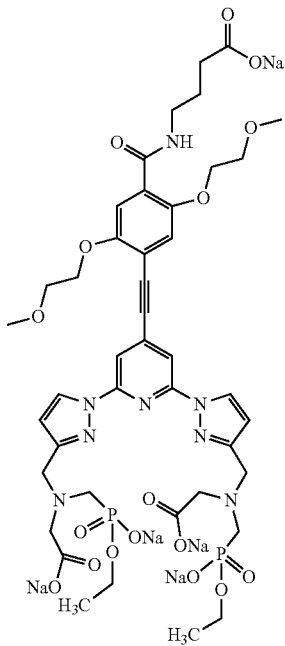
(I-5)
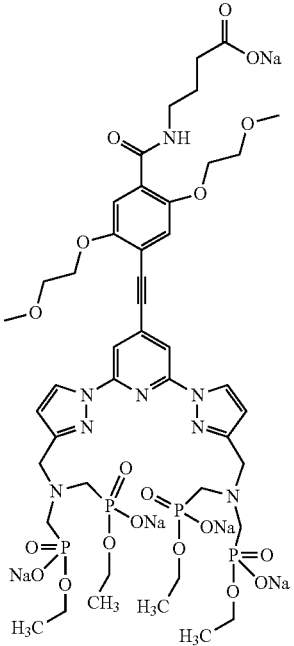
(I-7)

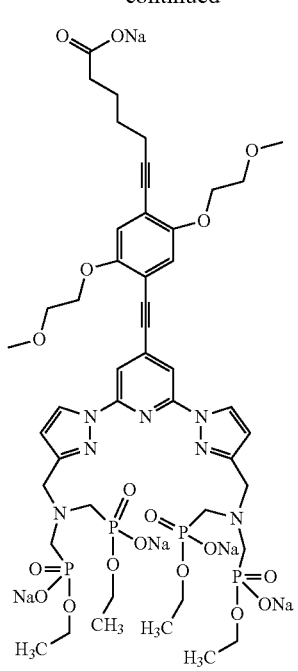

(I-8)

A complex of lanthanide or of a transition metal according to the invention comprises a lanthanide or transition metal ion, complexed with a ligand of formula (I) as defined previously. The lanthanide ion is chosen from the ions $Gd^{3+}$, $Lu^{3+}$, $Eu^{3+}$, $Tb^{3+}$, $Dy^{3+}$, $Sm^{3+}$, $Er^{3+}$, $Yb^{3+}$, $Pr^{3+}$ and $Nd^{3+}$. The ion of a transition metal may be chosen from the following metals Cu(II), Co(II), Mn(II or IV), Ni(II), Fe(III), Pd(II) and Pt(II).

A complex of lanthanide or of a transition metal may be obtained by mixing equimolar amounts of a compound of formula (I) (preferably in sodium salt form) with a lanthanide salt or, respectively, a transition metal salt, by heating the mixture, cooling and neutralizing to a pH of 6 to 8, followed by recovery of the complex at room temperature.

The lanthanide salt may be a nitrate, a chloride, a perchlorate or a triflate $Ln(CF_3SO_3)_3$.

The transition metal salt may be, for example, a chloride, acetate or nitrate or any other compound that is soluble in water or alcohols.

In one particular embodiment, the compound of formula (I) and the lanthanide salt or the transition metal salt are mixed in equimolar amounts as a solution in water or in an MeOH/water mixture, the solution is heated for 2 to 3 hours at 60° C., cooled to room temperature and then neutralized, if necessary, to pH 7 by addition of NaOH, a quaternary ammonium hydroxide or HCl diluted in water. The complexes formed are then isolated by concentration of the mother liquors and precipitation from an $H_2O/MeOH/THF/Et_2O$ mixture.

The complexes according to the invention have varied applications, depending on the nature of the substituents of the pyridyl group of the ligand. Their optical luminescence properties, the luminescence half-lives and the brightness properties are exceptional with virtually quantitative quantum yields (Tb(I-5) and Tb(I-7)) and half-lives of the excited states of greater than 3 milliseconds most of the time.

By way of example, all of the absorption and emission properties of the terbium complexes synthesized from ligands (I-1) to (I-4) in accordance with the invention are summarized in Table 1 below:

TABLE 1

| Nature of the complex | Absorption[a] | | Emission | | | |
|---|---|---|---|---|---|---|
| | $\lambda_{abs}$ (nm) | $\epsilon$ ($M^{-1}$, $cm^{-1}$) | $\tau$ (ms)[b] | | $\phi$ (%)[b] | |
| | | | $H_2O$ | $D_2O$ | $H_2O$ | $D_2O$ |
| Tb(I-5) | 283 | 45600 | 2.6 | 3.1 | 88 | 96 |
| | 328 | 10900 | | | | |
| Tb(I-6) | 275 | 50200 | 2.6 | 3.2 | 26 | 35 |
| | 328 | 12000 | | | | |
| Tb(I-7) | 284 | 44300 | 3.1 | 3.4 | 86 | 94 |
| | 328 | 10200 | | | | |
| Tb(I-8) | 272 | 45800 | 3.2 | 3.5 | 26 | 30 |
| | 327 | 11400 | | | | |

[a] in a 0.01M TRIS/HCl buffer at pH = 7.0.
[b] Error estimated at ±15% on the quantum yield and ±5% on the half-life τ.

The parameters $\phi$ and $\tau$ represent, respectively, the luminescence quantum yields and the luminescence half-lives. They may be measured in water and in $D_2O$.

In a preferred configuration of the invention, several stability tests show the absence of degradation of the fluorescent probe. It was demonstrated in particular that no loss of luminescence of the terbium complexes at $\lambda_{max}$ 490 and 543 nm and of europium complexes at $\lambda_{max}$ 590 and 620 nm was observed over several days when these complexes are dissolved in aqueous medium at neutral pH or in saline medium at concentrations of $10^{-4}$ to $10^{-6}$ M.

By way of example, the stability of the terbium complexes synthesized from ligands (I-1) to (I-4) in accordance with the invention in various buffers is given in Table 2 below. By way of comparison, Table 2 also gives the stability of a terbium complex TbL4 of the prior art corresponding to the following formula:

TbL4

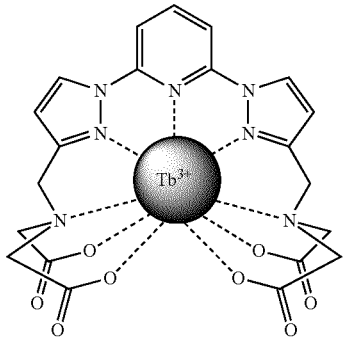

TABLE 2

| | $\tau$ (ms) Estimated error ± 5% on τ | | | | |
|---|---|---|---|---|---|
| Buffers | TbL4 * | Tb(I-5) | Tb(I-6) | Tb(I-7) | Tb(I-8) |
| $H_2O$ | 2.8 | 2.6 | 2.6 | 3.1 | 3.2 |
| Phosphate 0.1M. pH = 7.0 | 2.8 | 2.6 | 2.6 | 3.1 | 3.2 |
| Tris 0.1M. pH = 7.0 | 2.8 | 2.6 | 2.4 | 3.0 | 3.1 |
| Tris 0.1M-EDTA 10 mM. pH = 7.0 | 0.6 | 2.6 | 2.5 | 3.0 | 3.1 |
| Tris 50 mM-Serum 50% pH = 7.0 | 0.2 | 2.5 | 2.3 | 3.1 | 3.0 |
| Tris 0.1M-KF 400 mM. pH = 7.0 | 0 | 2.5 | 2.3 | 3.0 | 3.0 |

* complex not in accordance with the invention

This stability study shows that the complexes in accordance with the invention have excellent stability with half-lives of greater than 3 milliseconds in various aqueous media.

Moreover, the complexes in accordance with the invention have exceptional solubility in water. Their solubility ranges from 1 to 10 milligrams per milliliter of phosphate buffer.

Furthermore, the production and purification costs for these compounds make them very advantageous potential candidates for time-resolved biomedical and biological analysis for quantifying traces of analytes by specifically exciting the ligand which is considered as the photon-collecting antenna. The compounds in accordance with the invention make it possible to accommodate all of the lanthanides and the absorption properties of the ligands are modifiable as a function of the decoration provided by said ligand.

In particular, the complexes of the invention are useful for labeling compounds bearing an amine, alcohol, thiol, carboxylic acid or activated ester group. These compounds may be monomeric or polymeric molecules optionally in the form of beads. For this use, the group Z of the ligand of the complex is preferably a group —COOH, a group —COONa, an activated ester of the N-hydroxysuccinimide ester or pentafluorophenol ester type, a Br, an I, or an amine.

When the ligand of a luminescent complex bears a recognition site electronically linked to the complexation structure of the ligand, the luminescence properties of the complex may be disrupted by the presence of an analyte which binds to the recognition site. By electronically coupling the recognition site to the central pyridine via acetylenic bonds, the interaction of the recognition site with its substrates induces electronic disruptions that are reflected by changes in luminescence of the lanthanide ion complexes.

Two-photon absorption microscopy and spectroscopy are relatively recent techniques and have the advantage, especially in microscopy, of allowing a significant improvement in spatial resolution by using low-energy photons. Virtually all of the luminescent markers studied in two-photon absorption are fluorescent organic compounds of Rhodamine® type. These organic compounds have very low Stokes shifts and broad emission bands (corresponding to a half-height width of greater than 50 nm). The luminescent lanthanide ion complexes according to the present invention have very high Stokes shifts and narrow emission bands. They consequently constitute compounds that are particularly advantageous for biphotonic microscopy and labeling, and very recent studies have demonstrated this possibility on Eu and Tb complexes [cf. in particular a) Law, G. L.; et al. *J. Am. Chem. Soc.* 2008, 130, 3714; b) Picot, A.; et al., *J. Am. Chem. Soc.* 2008, 130, 1532.]. The complexes of the invention may be used as luminescent markers for two-photon absorption. For this particular application, the ligands I-1, I-2, I-3 and I-4 will preferentially be used.

The complexes of the invention in which the end group Z of the ligand is a biotin group are useful for recognizing avidin, streptavidin and neuravidin.

DETAILED DESCRIPTION

The present invention is illustrated by the following examples, to which it is not, however, limited.

Example 1

Synthesis of the Compound of Formula (I-1)

A compound of formula (I-1) was synthesized according to the following reaction scheme:

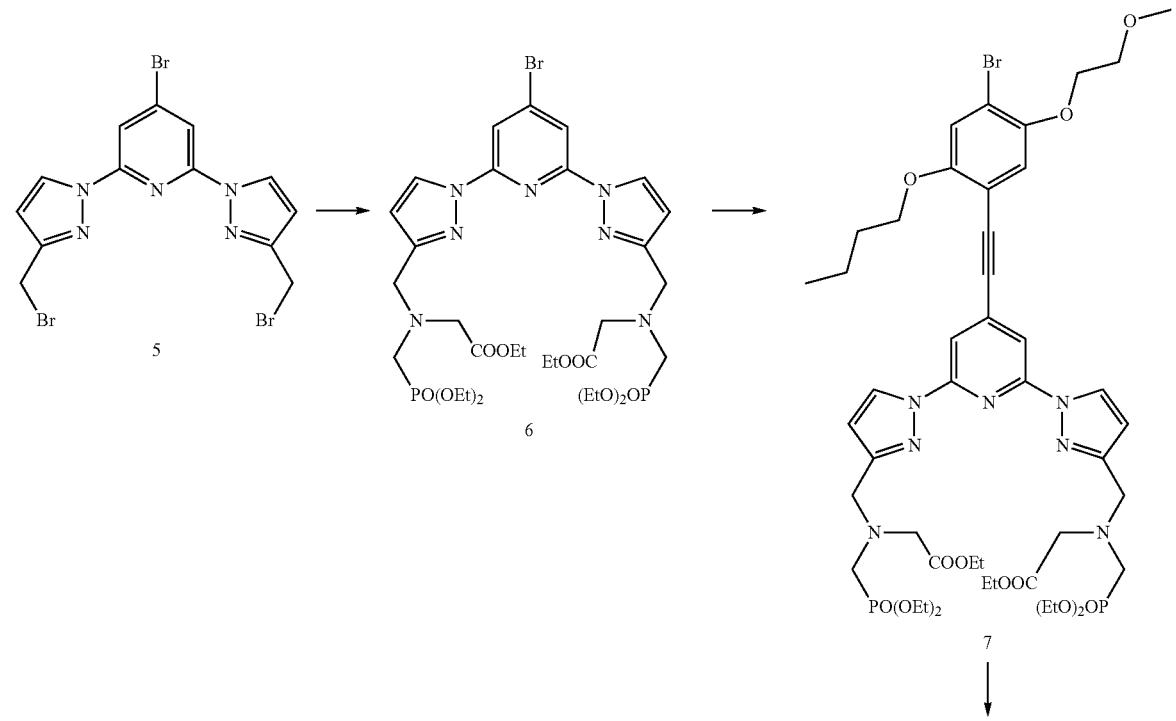

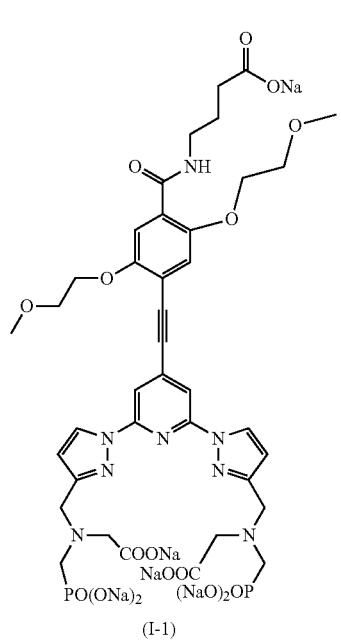

(I-1)

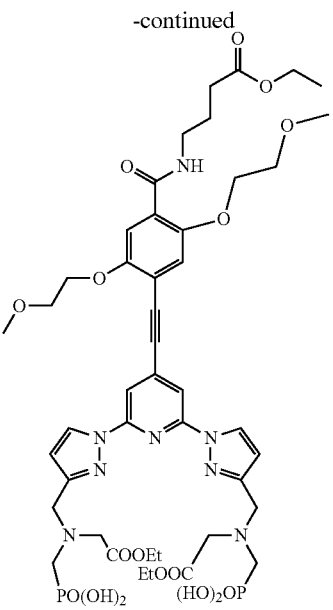

9

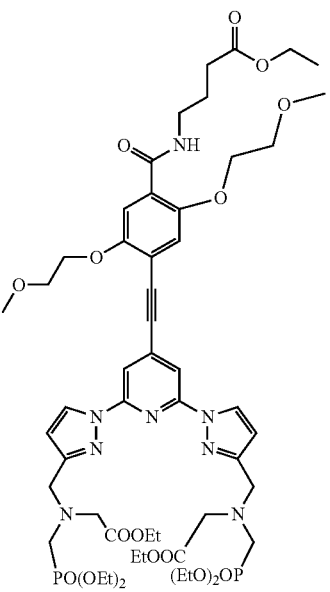

8

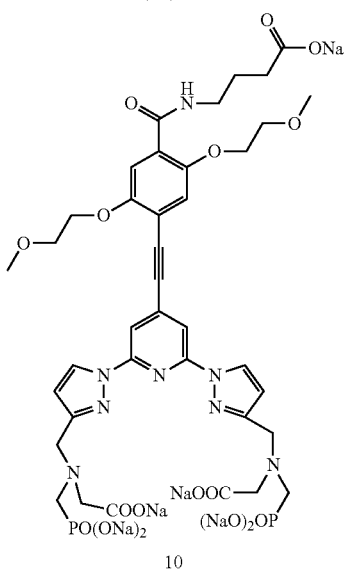

10

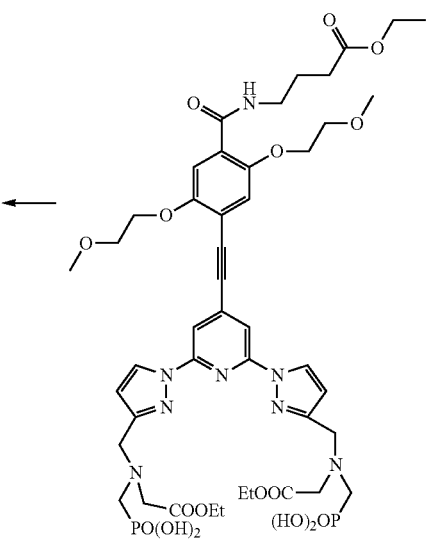

9

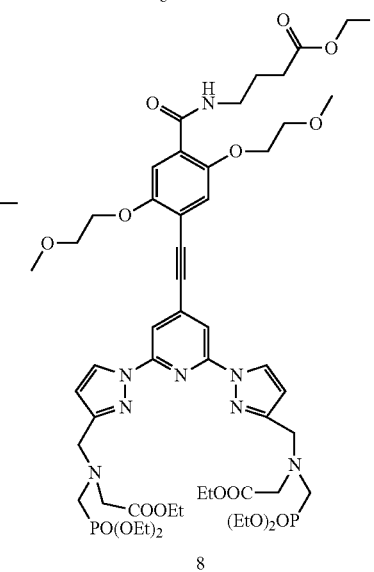

8

I) First Step: Synthesis of Compound 6

To a solution of compound 5 (prepared according to the reference P. Kadjane et al., Inorg. Chem., 2009, 48, 4601-4603) (267.6 mg, 0.562 mmol) in anhydrous acetonitrile (10 ml) were added 270.5 mg of glyphosate derivate of formula NH[PO(OEt)$_2$(COOEt)] (prepared according to the reference S. Aime et al., Chem. Eur. J. 2006, 6, 2609-2617) (1.068 mmol) and 310.8 mg of K$_2$CO$_3$ (2.249 mmol). The resulting solution was heated with stirring at 60° C. for 48 hours under argon. The product was purified by column chromatography on silica using a mixture of solvents (from 0/10 to 2/8 (v/v) MeOH/CH$_2$Cl$_2$). The expected compound 6 was obtained in the form of a white solid in a yield of 59%.

$^1$H NMR (300 MHz, CDCl$_3$) δ (ppm): 8.37 (d, J=2.6 Hz, 2H); 7.87 (s, 2H); 6.47 (d, J=2.6 Hz, 2H); 4.02-4.18 (m, 12H); 3.99 (s, 4H); 3.58 (s, 4H); 3.18 (s, 2H); 3.14 (s, 2H); 1.14-1.32 (m, 18H).

$^{31}$P {$^1$H} NMR (CDCl$_3$, 161 MHz): δ 24.52 ppm.

MS-ESI: 821.1 (98), 819.1 (100).

Elemental analysis for $C_{31}H_{48}N_7O_{10}P_2Br$:

|  | C | H | N |
| --- | --- | --- | --- |
| Calculated | 45.37 | 5.90 | 11.95 |
| Found | 45.09 | 5.76 | 11.76 |

2) Second Step: Synthesis of Compound 7

To a degassed solution of compound 6 obtained above in the preceding step (100 mg, 0.122 mmol) in a benzene/triethylamine mixture (5 ml/1 ml) were added 42.7 mg of compound 4 (0.130 mmol) and 10 mg of [Pd(PPh$_3$)$_4$]. The solution was heated at 60° C. overnight and the expected compound 7 was isolated by chromatography on silica as described above in step 1). The pure compound 7 was obtained in a yield of 79% in the form of a crystalline white solid.

$^1$H NMR (300 MHz, CDCl$_3$) δ (ppm): 8.35 (d, J=2.6 Hz, 2H) 7.84 (s, 2H); 6.81 (s, 1H); 6.73 (s, 1H); 6.45 (d, J=2.6 Hz, 2H); 4.13 (m, 4H); 4.09-4.17 (m, 12H); 4.04 (s, 4H); 3.85 (m, 4H); 3.27 (s, 6H); 3.64 (s, 4H); 3.23 (s, 2H); 3.17 (s, 2H); 1.14-1.32 (m, 18H).

$^{31}$P {$^1$H} NMR (CDCl$_3$, 161 MHz): δ 24.47 ppm.

MS-ESI: 1069.2 (95), 1067.2 (100).

Elemental analysis for C$_{45}$H$_{64}$N$_7$O$_{14}$P$_2$Br:

|  | C | H | N |
|---|---|---|---|
| Calculated | 50.57 | 6.04 | 9.17 |
| Found | 50.32 | 5.96 | 8.86 |

3) Third Step: Synthesis of Compound 8

To a solution of 115.0 mg of compound 7 obtained above in the preceding step (0.107 mmol) in a toluene (8 ml)/triethylamine (8 ml) mixture were added 51.7 mg of 4-ethylaminobutyrate hydrochloride (0.308 mmol) and 9.8 mg of Pd(PPh$_3$Cl$_2$) (0.014 mmol). The resulting solution was heated at 70° C. for 12 hours under continuous reflux of CO. The expected compound 8 was obtained in the form of a white solid after purification by chromatography on silica gel with a mixture of solvents as eluent (from 0/10 to 4/6 MeOH/CH$_2$Cl$_2$). A yield of 56% was obtained.

$^1$H NMR (200 MHz, CDCl$_3$) δ (ppm): 8.44 (d, J=2.6 Hz, 2H); 8.21 (s, 2H); 7.50 (m, 1H); 6.80 (s, 1H); 6.70 (s, 1H); 6.49 (d, J=2.6 Hz, 2H); 4.15 (m, 4H); 4.06-4.19 (m, 12H); 4.04 (s, 4H); 3.82 (m, 4H); 3.65 (s, 4H); 3.52 (m, 4H); 3.27 (s, 6H); 3.24 (s, 2H); 3.20 (s, 2H); 2.43 (t, J=7.0 Hz, 2H); 1.98 (q, J=7.0 Hz, 2H); 1.15-1.37 (m, 21H).

$^{31}$P {$^1$H} NMR (CDCl$_3$, 161 MHz) δ 24.56 ppm.

MS-ESI: 1146.3 (100).

Elemental analysis for C$_{52}$H$_{76}$N$_8$O$_{17}$P$_2$:

|  | C | H | N |
|---|---|---|---|
| Calculated | 54.44 | 6.68 | 9.77 |
| Found | 54.13 | 6.43 | 9.56 |

4) Fourth Step: Synthesis of Compound 9

To an aqueous suspension of 70.0 mg of compound 8 obtained above in the preceding step (0.061 mmol) in 2 ml of water were added 5 ml of 6N hydrochloric acid and the resulting mixture was heated at 60° C. for 3 days. The expected compound 9 was obtained by precipitation from ether, in a yield of 77%.

$^1$H NMR (200 MHz, MeOD+D$_2$O) δ (ppm) 8.80 (s, 2H); 8.21 (d, J=8.0 Hz, 2H); 6.83 (s, 2H); 6.76 (s, 1H); 6.65 (s, 1H); 4.85 (s, 4H); 4.39 (s, 4H); 4.09 (m, 4H); 3.78 (m, 4H); 3.74-3.96 (m, 5H); 3.26 (s, 6H); 3.18 (q, J=7.0 Hz, 8H); 2.34-2.53 (m, 2H); 1.93 (m, 2H); 1.29 (t, J=7.0 Hz, 9H).

$^{31}$P {$^1$H} NMR (CD$_3$OD, 161 MHz): δ 8.70 ppm.

MS-ESI: 1035.4 (100).

Elemental analysis for C$_{44}$H$_{60}$N$_8$O$_{17}$P$_2$, HCl:

|  | C | H | N |
|---|---|---|---|
| Calculated | 50.57 | 5.89 | 9.82 |
| Found | 50.16 | 5.56 | 9.65 |

5) Fifth Step: Synthesis of Compound (I-1)

To a solution of 40.9 mg of compound 9 (0.052 mmol) in water (6 ml) at pH 7.0 were added 8.3 mg of NaOH (0.208 mmol) and the solution was stirred at room temperature for 24 hours. The expected compound (I-1) was obtained by precipitation from ether, in a yield of 76%.

$^1$H NMR (300 MHz, D$_2$O) δ (ppm): 8.67 (s, 2H) 7.98 (d, J=8.0 Hz, 2H); 6.75 (s, 2H); 6.76 (s, 1H); 6.65 (s, 1H); 4.81 (s, 4H); 4.32 (s, 4H); 4.11 (m, 4H); 3.79 (m, 4H); 3.70-4.00 (m, 4H); 3.24 (s, 6H); 3.14 (m, 2H); 2.30-2.65 (m, 2H); 1.97 (m, 2H).

$^{31}$P{$^1$H} NMR (CD$_3$OD+D$_2$O, 161 MHz): δ 16.41 ppm.

MS-ESI (methanol+2% TfA) 476.1 ([M$^{2+}$], 100), 951.2 ([M$^+$], 55).

Elemental analysis for C$_{38}$H$_{41}$N$_8$Na$_7$O$_{17}$P$_2$, 2H$_2$O:

|  | C | H | N |
|---|---|---|---|
| Calculated | 40.01 | 3.98 | 9.82 |
| Found | 39.79 | 3.68 | 9.67 |

Example 2

Synthesis of the Compound of Formula (I-2)

A compound of formula (I-2) was synthesized according to the following reaction scheme:

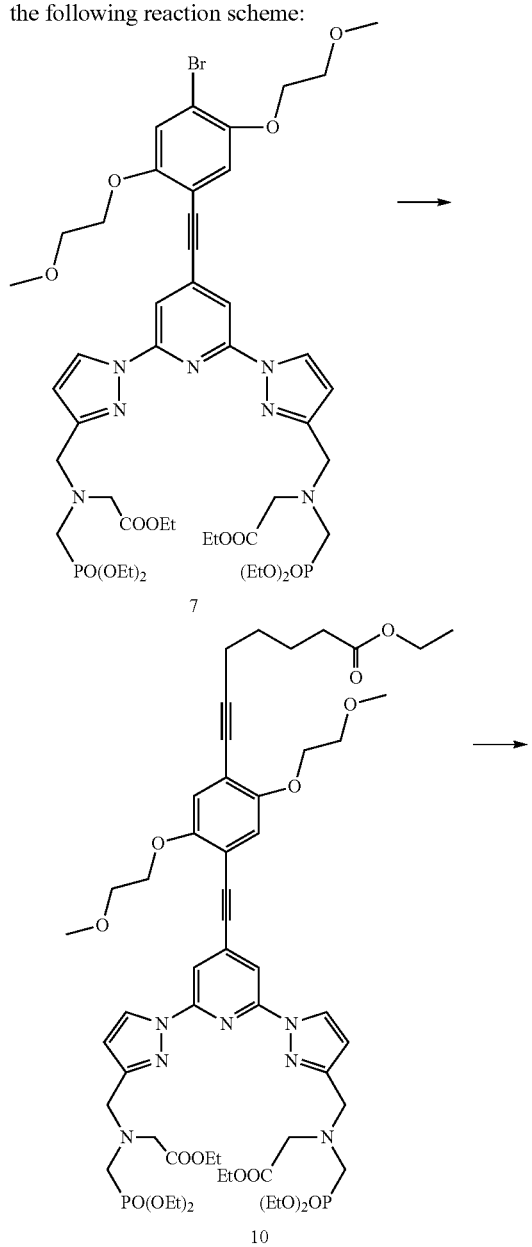

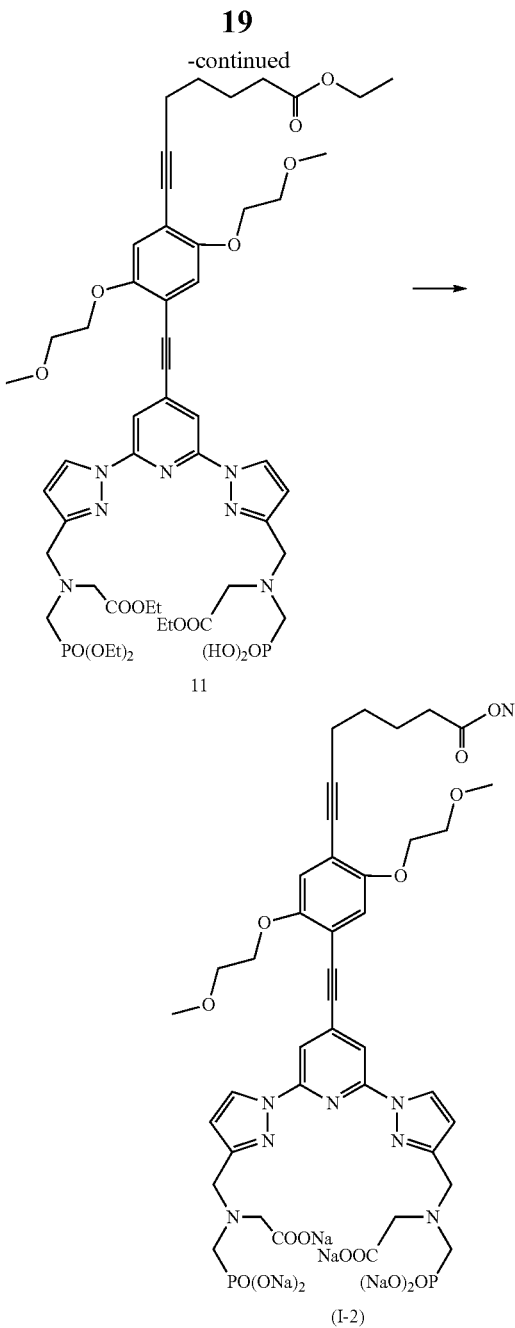

1) First Step: Synthesis of Compound 10

To a degassed solution of 175.2 mg of compound 7 as prepared above in step 2) of Example 1 above (0.164 mmol) in a mixture of 6 ml of tetrahydrofuran and 2 ml of triethylamine were successively added 15.0 mg of Pd(PPh$_3$Cl$_2$) (0.021 mmol), 4.1 mg of CuI (0.021 mmol) and 98.8 mg of ethyl 6-heptynoate (0.641 mmol). The solution was heated at 50° C. for 12 hours. The product was purified by chromatography using a variable mixture of dichloromethane/methanol (from 0/10 to 4/6 (v/v) MeOH/CH$_2$Cl$_2$) to give the expected compound 10 in the form of a white solid, in a chemical yield of 80%.

$^1$H NMR (300 MHz, CDCl$_3$) δ (ppm): 8.41 (s, 2H); 7.70 (s, 2H); 6.85 (s, 1H); 6.75 (s, 1H); 6.48 (s, 2H); 4.15 (m, 4H); 4.05-4.20 (m, 14H); 4.01 (s, 4H); 3.78 (m, 4H); 3.62 (s, 4H); 3.21 (m, 8H); 3.17 (s, 2H); 2.45 (t, J=7.0 Hz, 2H); 2.33 (t, J=7.0 Hz, 2H); 1.76 (q, J=7.0 Hz, 2H); 1.65 (q, J=7.0 Hz, 2H); 1.11-1.34 (m, 21H).

$^{31}$P {$^1$H} NMR (CDCl$_3$, 161 MHz): δ 28.44 ppm.
MS-ESI 1141.3 (100).
Elemental analysis for C$_{54}$H$_{77}$N$_7$O$_{16}$P$_2$

|  | C | H | N |
|---|---|---|---|
| Calculated | 56.78 | 6.80 | 8.58 |
| Found | 56.53 | 6.52 | 8.33 |

2) Second Step: Synthesis of Compound 11

To a solution of 134.8 mg of compound 10 obtained above in the preceding step (0.118 mmol) in 10 ml of anhydrous acetonitrile were added 1.154 g of distilled trimethylsilyl bromide (7.540 mmol) and 0.807 g of anhydrous 2,6-lutidine (7.540 mmol). The resulting solution was stirred at room temperature for 48 hours under argon. After evaporating off the solvent, the residue was dissolved in water and the pH was adjusted to 7.0 with aqueous sodium hydroxide solution (0.1M to 0.01M). The expected compound 11 was obtained by precipitation of a methanol solution with diethylether. Compound 11 was thus obtained in a yield of 83%.

$^1$H NMR (200 MHz, MeOD) δ (ppm): 8.75 (s, 2H); 7.78 (s, 2H); 6.82 (s, 1H); 6.77 (s, 2H); 6.71 (s, 1H); 4.68 (s, 4H); 4.13 (m, 4H); 4.20-4.35 (m, 10H); 3.82 (m, 4H); 3.27 (t, 4H); 3.48 (s, 2H); 3.42 (s, 2H); 2.58 (t, J=7.0 Hz, 2H); 2.42 (t, J=7.0 Hz, 2H); 1.60-1.92 (m, 4H); 1.16-1.38 (m, 9H).

$^{31}$P {$^1$H} NMR (CD$_3$OD+D$_2$O, 161 MHz): δ 8.56 ppm.
MS-ESI 1029.3 (100).
Elemental analysis for C$_{46}$H$_{61}$N$_7$O$_{16}$P$_2$

|  | C | H | N |
|---|---|---|---|
| Calculated | 53.64 | 5.97 | 9.52 |
| Found | 53.64 | 5.66 | 9.21 |

3) Third Step: Synthesis of Compound (I-2)

To a solution of 131.1 mg of compound 11 obtained above in the preceding step (0.127 mmol) in 4 ml of water were added 60.4 mg of sodium hydroxide (0.151 mmol). The resulting solution was stirred at room temperature for 12 hours. After evaporating to dryness, the compound was precipitated with ether from a methanol solution. The expected compound (I-2) was thus obtained in a yield of 72%.

$^1$H NMR (200 MHz, D$_2$O) δ (ppm): 8.47 (s, 2H); 7.45 (s, 2H); 6.82 (s, 1H); 6.73 (s, 1H); 6.65 (s, 2H); 4.11 (m, 4H); 3.90 (s, 4H); 3.80 (m, 4H); 3.33 (s, 4H); 3.26 (s, 6H); 2.41-2.78 (m, 6H); 2.16-2.40 (m, 2H); 1.49-1.88 (m, 4H).

$^{31}$P {$^1$H} NMR (CD$_3$OD+D$_2$O, 161 MHz): δ 17.09 ppm.
MS-ESI (methanol+2% TfA) 473.1 ([M$^{2+}$], 100), 946.2 ([M$^+$], 55).
Elemental analysis for C$_{40}$H$_{42}$N$_7$Na$_7$O$_{16}$P$_2$, 2 H$_2$O

|  | C | H | N |
|---|---|---|---|
| Calculated | 42.30 | 4.08 | 8.63 |
| Found | 42.09 | 3.84 | 8.43 |

Example 3

Synthesis of the Compound of Formula (I-4)

A compound I-4 was synthesized according to the following reaction scheme:

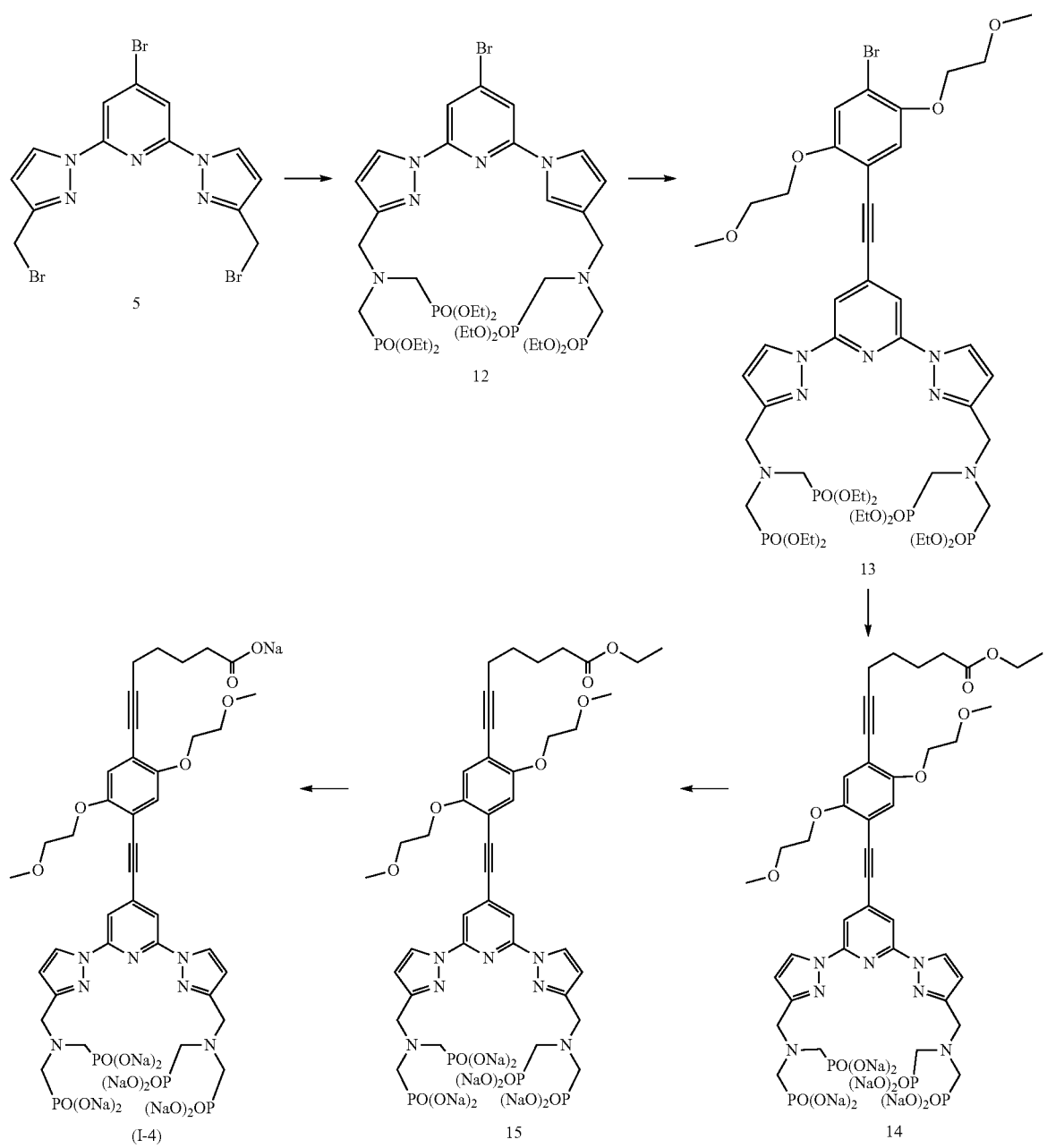

1) First Step: Synthesis of Compound 12

To a solution of 256.4 mg of compound 5 as used above in the first step of Example 1 (0.539 mmol) in 10 ml of anhydrous acetonitrile were added 512.7 mg of derivative aminobis(methylenediethyl phosphite) (1.616 mmol) and 297.8 mg of anhydrous $K_2CO_3$ (2.155 mmol). The resulting suspension was heated at 60° C. for 12 hours under argon. The compound was purified by chromatography on silica gel, using a mixture of solvents (from 0/10 to 4/6 (v/v) $MeOH/CH_2Cl_2$) to give the expected compound 12 in the form of a white solid, in a yield of 65%.

$^1$H NMR (300 MHz, $CDCl_3$) δ (ppm): 8.36 (d, J=2.6 Hz, 2H); 7.87 (s, 2H); 6.48 (d, J=2.6 Hz, 2H); 4.01-4.14 (m, 20H); 3.16 (s, 4H); 3.12 (s, 4H); 1.25 (t, J=7.0 Hz, 24H).

$^{31}$P {$^1$H} NMR ($CDCl_3$, 161 MHz): δ 24.76 ppm.

MS-ESI 949.1 (100), 947.1 (90).

Elemental analysis for $C_{33}H_{58}N_7O_{12}P_4Br$:

| | C | H | N |
|---|---|---|---|
| Calculated | 41.78 | 6.16 | 10.34 |
| Found | 41.34 | 6.00 | 10.09 |

2) Second Step: Synthesis of Compound 13

To a degassed solution of 100 mg of compound 12 obtained above in the preceding step (0.105 mmol) in a benzene/triethylamine mixture (5 ml/1 ml) were added 41.6 mg of compound 4 (0.126 mmol) and 10 mg of [Pd(PPh$_3$)$_4$]. The solution was heated at 60° C. overnight, and the expected compound 13 was isolated by chromatography on silica. The pure compound was obtained in a yield of 83% in the form of a crystalline white solid.

$^1$H NMR (300 MHz, CDCl$_3$) δ (ppm): 8.42 (d, J=2.7 Hz, 2H); 7.96 (s, 2H); 6.80 (s, 1H); 6.74 (s, 1H); 6.53 (d, J=2.7 Hz, 2H); 4.13 (m, 4H); 4.01-4.14 (m, 20H); 3.80 (m, 4H); 3.27 (s, 6H); 3.17 (s, 4H); 3.12 (s, 4H); 1.27 (t, J=7.0 Hz, 24H).

$^{31}$P {$^1$H} NMR (CDCl$_3$, 161 MHz): δ 24.87 ppm.

MS-ESI 1197.2 (100), 1195.2 (90).

Elemental analysis for C$_{47}$H$_{74}$N$_7$O$_{16}$P$_4$Br:

|  | C | H | N |
| --- | --- | --- | --- |
| Calculated | 47.16 | 6.23 | 8.19 |
| Found | 46.87 | 6.02 | 7.76 |

3) Third Step: Synthesis of Compound 14

To a solution of 122.2 mg of compound 13 obtained above in the preceding step (0.102 mmol) in a mixture of 6 ml of tetrahydrofuran and 2 ml of triethylamine were added 9.0 mg of Pd(PPh$_3$)$_2$Cl$_2$ (0.013 mmol) and 2.5 mg of CuI (0.013 mmol) and also 39.7 mg of ethyl hept-6-ynoate (0.258 mmol). The resulting solution was heated at 50° C. for 36 hours under argon. The product was purified by chromatography on silica gel, with an eluent comprising (from 0/10 to 6/4 (v/v) MeOH/CH$_2$Cl$_2$) to give the expected compound 14 in the form of a white solid, in a chemical yield of 75%.

$^1$H NMR (400 MHz, CDCl$_3$) δ (ppm): 8.42 (d, J=2.6 Hz, 2H); 7.70 (s, 2H); 6.80 (s, 1H); 6.75 (s, 1H); 6.50 (d, J=2.6 Hz, 2H); 4.14 (m, 4H); 3.85 (m, 4H); 4.06-4.16 (m, 22H); 3.25 (s, 6H); 3.20 (s, 4H); 3.18 (s, 4H); 2.46 (t, J=7.0 Hz, 2H); 2.33 (t, J=7.2 Hz, 2H); 1.72-1.82 (m, 2H); 1.60-1.70 (m, 2H); 1.29 (t, J=7.0 Hz, 24H); 1.22 (t, J=7.0 Hz, 3H).

$^{31}$P {$^1$H} NMR (CDCl$_3$, 161 MHz): δ 24.89 ppm.

MS-ESI 1269.4 (100).

Elemental analysis for C$_{56}$H$_{87}$N$_7$O$_{18}$P$_4$:

|  | C | H | N |
| --- | --- | --- | --- |
| Calculated | 52.95 | 6.90 | 7.72 |
| Found | 52.67 | 6.53 | 7.45 |

4) Fourth Step: Synthesis of Compound 15

To a solution of 99.0 mg of compound 14 obtained above in the preceding step (0.078 mmol) in 10 ml of anhydrous acetonitrile were added 1.483 g of freshly distilled trimethylsilyl bromide (9.687 mmol) and 1.038 g of anhydrous 2,6-lutidine (9.687 mmol). The resulting solution was stirred at room temperature for 48 hours under argon. After this time, the solution was evaporated to dryness, the residue was dissolved in water and the pH of the solution was adjusted to 7 with sodium hydroxide solution (0.1M to 0.01M). The expected compound 15 was obtained in a chemical yield of 68%.

$^1$H NMR (200 MHz, D$_2$O) δ (ppm): 8.44 (s, 2H); 7.38 (s, 2H); 6.86 (s, 2H); 6.80 (s, 1H); 6.76 (s, 1H); 4.20-4.38 (m, 2H); 4.16 (m, 4H); 3.87 (m, 4H); 4.09 (t, 4H); 3.76 (t, 4H); 3.46-3.78 (s, 12H); 3.26 (s, 6H); 2.48-2.70 (m, 4H); 1.62-2.00 (m, 4H); 1.28-1.48 (m, 3H).

$^{31}$P {$^1$H} NMR (CD$_3$OD+D$_2$O, 161 MHz): δ 8.44 ppm.

MS-ESI 1045.1 (100).

Element analysis for C$_{40}$H$_{55}$N$_7$O$_{18}$P$_4$:

|  | C | H | N |
| --- | --- | --- | --- |
| Calculated | 45.94 | 5.30 | 9.38 |
| Found | 45.65 | 5.08 | 9.12 |

5) Fifth Step: Synthesis of Compound (I-4)

To a solution of 94.3 mg of compound 15 obtained above in the preceding step (0.090 mmol) in 4 ml of water were added 31.0 mg of sodium hydroxide (0.775 mmol). The solution was stirred under argon at room temperature for 24 hours. After evaporating off the solvent, the residue was dissolved in methanol and the compound was precipitated with ether. 95% of the analytically pure expected compound (I-4) were recovered.

$^1$H NMR (200 MHz, D$_2$O) δ (ppm): 8.68 (s, 2H); 7.70 (s, 2H); 6.87 (s, 2H); 6.80 (s, 1H); 6.75 (s, 1H); 4.17 (s, 4H); 4.12 (m, 4H); 3.76 (m, 4H); 3.26 (s, 6H); 2.84 (s, 4H); 2.78 (s, 4H); 2.54-2.70 (m, 2H); 2.28-2.42 (m, 2H); 1.60-1.94 (m, 4H).

$^{31}$P {$^1$H} NMR (CD$_3$OD+D$_2$O, 161 MHz): δ 16.53 ppm.

MS-ESI (methanol+2% TfA) 509.5 ([M$^{2+}$], 100), 1018.1 ([M$^+$], 35).

Elemental analysis for C$_{38}$H$_{42}$N$_7$Na$_9$O$_{18}$P$_4$, 2 H$_2$O:

|  | C | H | N |
| --- | --- | --- | --- |
| Calculated | 36.47 | 3.70 | 7.83 |
| Found | 36.14 | 3.43 | 7.58 |

Example 4

Synthesis of the Compound of Formula (I-3)

A compound of formula (I-3) was synthesized according to the following reaction scheme:

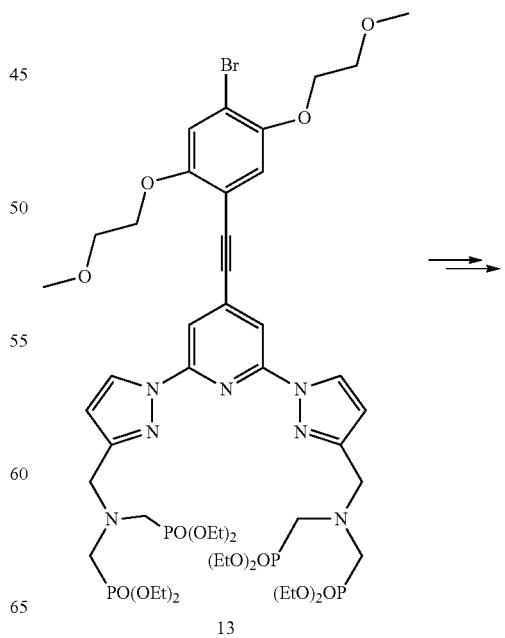

13

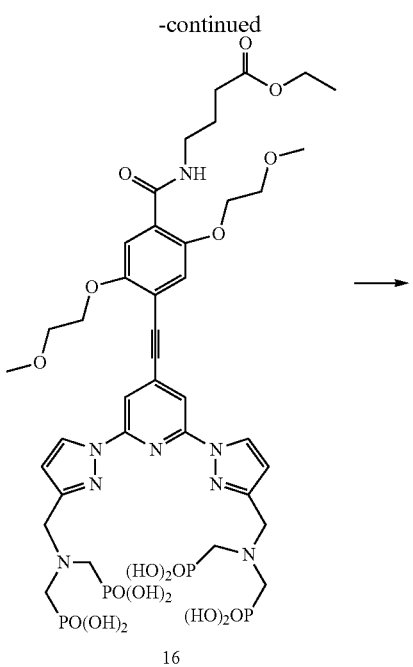

16 of CO. At the end of the reaction, the solvent was evaporated off and the residue was treated with water and extracted with dry dichloromethane. The white solid was dried and dissolved in anhydrous acetonitrile (10 ml), 740 mg of freshly distilled trimethylsilyl bromide (4.84 mmol) and 519 mg of anhydrous 2,6-lutidine (4.843 mmol) were added thereto. The resulting solution was stirred at room temperature for 48 hours under argon. The solution was evaporated to dryness, the residue was dissolved in water and the pH of the solution was adjusted to 7 with sodium hydroxide solution (0.1M to 0.01M). The expected compound 16 was obtained in a chemical yield of 58% for the two synthetic steps.

$^1$H NMR (200 MHz, D$_2$O) δ (ppm): 8.58 (s, 2H); 7.46 (s, 2H); 6.86 (s, 2H); 6.80 (s, 1H); 6.76 (s, 1H); 4.15 (m, 4H); 4.09 (m, 4H); 3.76 (t, 4H); 3.46-3.78 (m, 8H); 3.26 (s, 6H); 2.48-2.70 (m, 3H); 1.62-2.00 (m, 4H); 1.28-1.48 (m, 3H); 3.65 (s, 4H); 3.26 (s, 2H); 3.20 (s, 2H); 2.43 (t, J=7.0 Hz, 2H).

$^{31}$P {$^1$H} NMR (CD$_3$OD+D$_2$O, 161 MHz): δ 8.78 ppm.

MS-ESI 1050.1 (100).

Elemental analysis for C$_{38}$H$_{54}$N$_8$O$_{19}$P$_4$:

|  | C | H | N |
|---|---|---|---|
| Calculated | 43.44 | 5.18 | 10.66 |
| Found | 43.09 | 4.76 | 10.23 |

2) Second Step: Synthesis of Compound (I-3)

To a solution of 94.3 mg of compound 16 obtained above in the preceding step (0.090 mmol) in 4 ml of water were added 31.0 mg of sodium hydroxide (0.775 mmol). The solution was stirred under argon at room temperature for 24 hours. After evaporating off the solvent, the residue was dissolved in methanol and the compound was precipitated out with ether, 95% of the analytically pure expected compound (I-3) were recovered.

$^1$H NMR (200 MHz, D$_2$O) δ (ppm): 8.62 (s, 2H); 7.53 (s, 2H); 6.83 (s, 2H); 6.78 (s, 1H); 6.77 (s, 1H); 4.20 (t, 4H); 4.11 (m, 4H); 3.74 (m, 4H); 3.32 (s, 6H); 2.52-2.83 (m, 4H); 3.71 (s, 4H); 3.31 (s, 2H); 3.19 (s, 2H); 1.41-1.61 (m, 3H).

$^{31}$P {$^1$H} NMR (D$_2$O, 161 MHz): δ 15.97 ppm.

MS-ESI (methanol+2% TfA) 509.5 ([M2+], 100), 1018.1 ([M+], 35).

Elemental analysis for C$_{36}$H$_{41}$N$_8$Na$_9$O$_{19}$P$_4$, 2H$_2$O:

|  | C | H | N |
|---|---|---|---|
| Calculated | 34.41 | 3.61 | 8.92 |
| Found | 34.17 | 3.21 | 8.78 |

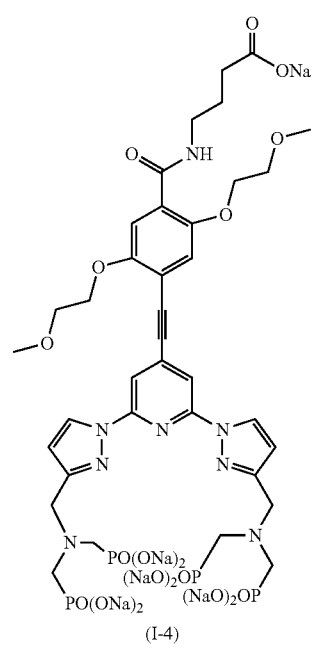

(I-4)

1) First Step: Synthesis of Compound 16

To a solution of 115.0 mg of compound 13 obtained above in step 2) of Example 3 (0.096 mmol) in a mixture of 8 ml of toluene and 8 ml of triethylamine were added 51.7 mg of 4-ethylaminobutyrate hydrochloride (0.308 mmol) and 9.8 mg of Pd(PPh$_3$)$_2$Cl$_2$ (0.014 mmol). The resulting solution was heated at 70° C. for 12 hours under a continuous stream Example 5

Synthesis of the Compound of Formula (I-5)

A compound of formula (I-5) was synthesized according to the following reaction scheme:

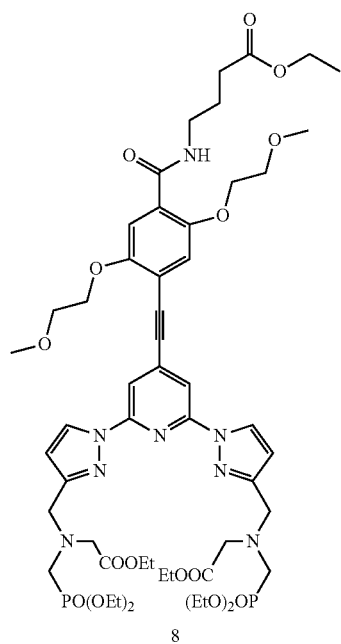

8

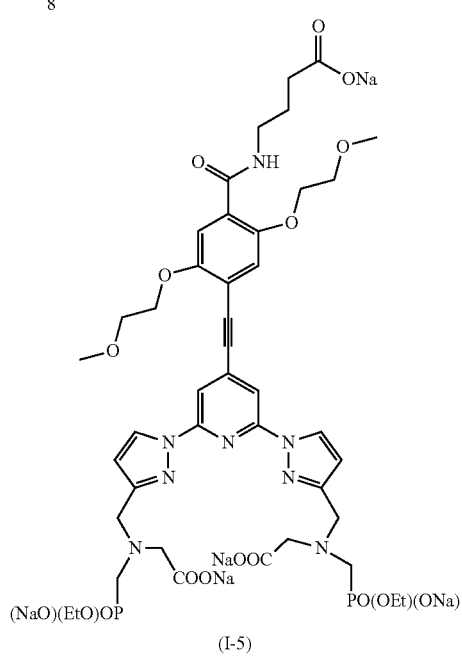

(I-5)

To a solution of compound 8 (50 mg, 0.044 mmol) obtained above in the third step for preparing the compound of formula (I-1), in water (10 ml), were added 5 ml of aqueous 1M sodium hydroxide solution. The solution was stirred at room temperature for 12 hours. Slow addition of diethylether brought about precipitation of the desired compound (I-5). This precipitate was centrifuged at 3000 rpm, and washed with ether. The resulting compound was recrystallized twice by diffusion of ether into a concentrated methanol solution. The expected compound of formula (I-5) was obtained in a yield of 83%.

$^1$H NMR (300 MHz, D$_2$O) δ (ppm): 8.62 (s, 2H) 8.03 (d, J=8.0 Hz, 2H); 6.78 (s, 2H); 6.81 (s, 1H); 6.72 (s, 1H); 4.83 (s, 4H); 4.34 (s, 4H); 4.14 (m, 4H); 3.82 (m, 4H); 3.62 (m, 4H); 3.62-4.04 (m, 4H); 3.18 (s, 6H); 3.15 (m, 2H); 2.32-2.63 (m, 2H); 1.92 (m, 2H); 1.12 (m, 6H).

$^{31}$P{$^1$H} NMR (CD$_3$OD+D$_2$O, 161 MHz): δ 28.21 ppm.
MS-ESI (methanol+2% TfA) 1007.2 ([M$^+$], 100).

Elemental analysis for C$_{42}$H$_{51}$N$_8$Na$_5$O$_{17}$P$_2$, 2H$_2$O:

|  | C | H | N |
|---|---|---|---|
| Calculated | 43.76 | 4.81 | 9.72 |
| Found | 43.64 | 4.49 | 9.53 |

Example 6

Synthesis of the Compound of Formula (I-6)

A compound of formula (I-6) was synthesized according to the following reaction scheme:

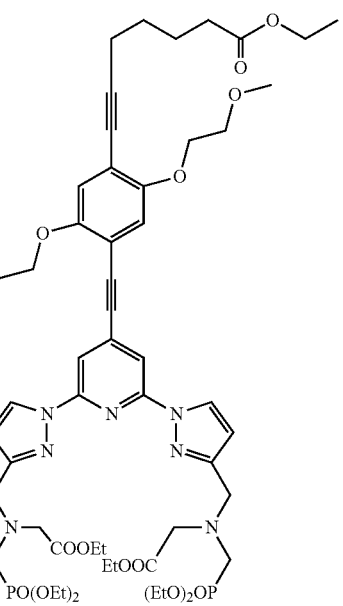

10

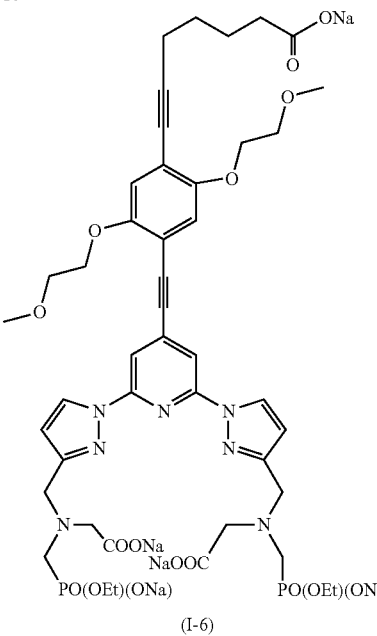

(I-6)

To a solution of compound 10 (50 mg, 0.044 mmol) obtained above in the first step for preparing the compound of formula (I-2), in water (10 ml), were added 5 ml of aqueous sodium hydroxide solution (1N). The solution was stirred at room temperature for 12 hours. Slow addition of diethylether brought about precipitation of the desired compound (I-6). This precipitate was centrifuged at 3000 rpm, and washed with ether. The resulting compound was recrystallized twice by diffusion of ether into a concentrated methanol solution. The expected compound of formula (I-6) was obtained in a yield of 82%.

$^1$H NMR (200 MHz, D$_2$O) δ (ppm): 8.49 (s, 2H); 7.53 (s, 2H); 6.76 (s, 1H); 6.97 (s, 1H); 6.83 (s, 2H); 4.21 (m, 4H); 3.87 (s, 4H); 3.83 (m, 4H); 3.52 (m, 4H), 3.36 (s, 4H); 3.28 (s, 6H); 2.36-2.81 (m, 6H); 2.22-2.41 (m, 2H) 1.52-1.91 (m, 4H), 1.13 (m, 6H).

$^{31}$P {$^1$H} NMR (CD$_3$OD+D$_2$O, 161 MHz): δ 28.19 ppm.

MS-ESI (methanol+2% TfA) 1002.2 ([M$^{3\ominus}$], 100).

Elemental analysis for C$_{44}$H$_{52}$N$_7$Na$_5$O$_{16}$P$_2$, 2H$_2$O

|  | C | H | N |
|---|---|---|---|
| Calculated | 46.04 | 4.92 | 8.54 |
| Found | 45.74 | 3.65 | 8.16 |

Example 7

Synthesis of the Compound of Formula (I-8)

A compound of formula (I-8) was synthesized according to the following reaction scheme:

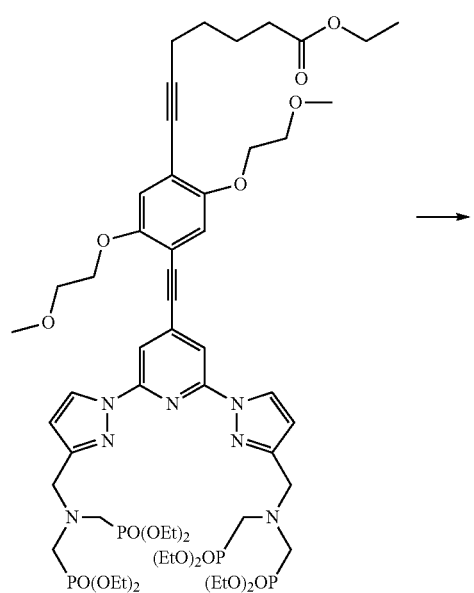

14

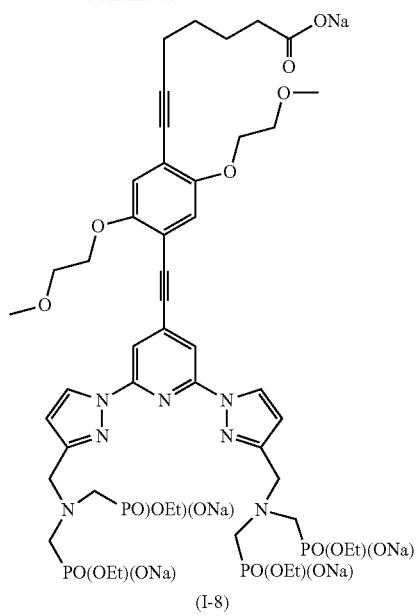

(I-8)

To a solution of compound 14 (50 mg, 0.039 mol) obtained above in the third step for preparing the compound of formula (I-4), in water (5 ml), were added 5 ml of aqueous sodium hydroxide solution (1N). The solution was stirred at room temperature for 12 hours. Slow addition of diethylether brought about precipitation of the desired compound (I-6). This precipitate was centrifuged at 3000 rpm and washed with ether. The resulting compound was recrystallized twice by diffusion of ether into a concentrated methanol solution. The expected compound of formula (I-8) was obtained in a yield of 76%.

$^1$H NMR (200 MHz, D$_2$O) δ (ppm): 8.63 (s, 2H); 7.64 (s, 2H); 6.82 (s, 2H); 6.76 (s, 1H); 6.65 (s, 1H); 4.15 (s, 4H); 4.10 (m, 4H); 3.71 (m, 4H); 3.52 (m, 8H), 3.21 (s, 6H); 2.79 (s, 4H); 2.74 (s, 4H); 2.49-2.73 (m, 2H); 2.25-2.39 (m, 2H); 1.58-1.88 (m, 4H), 1.12 (m, 12H).

$^{31}$P {$^1$H} NMR (CD$_3$OD+D$_2$O, 161 MHz): δ 28.23 ppm.

MS-ESI (methanol+2% TfA) 1130.2 ([M$^+$], 100).

Elemental analysis for C$_{46}$H$_{62}$N$_7$Na$_5$O$_{18}$P$_4$, 2H$_2$O:

|  | C | H | N |
|---|---|---|---|
| Calculated | 43.30 | 5.21 | 7.68 |
| Found | 43.10 | 4.93 | 7.43 |

Example 8

Synthesis of the Compound of Formula (I-7)

A compound of formula (I-7) was synthesized according to the following reaction scheme:

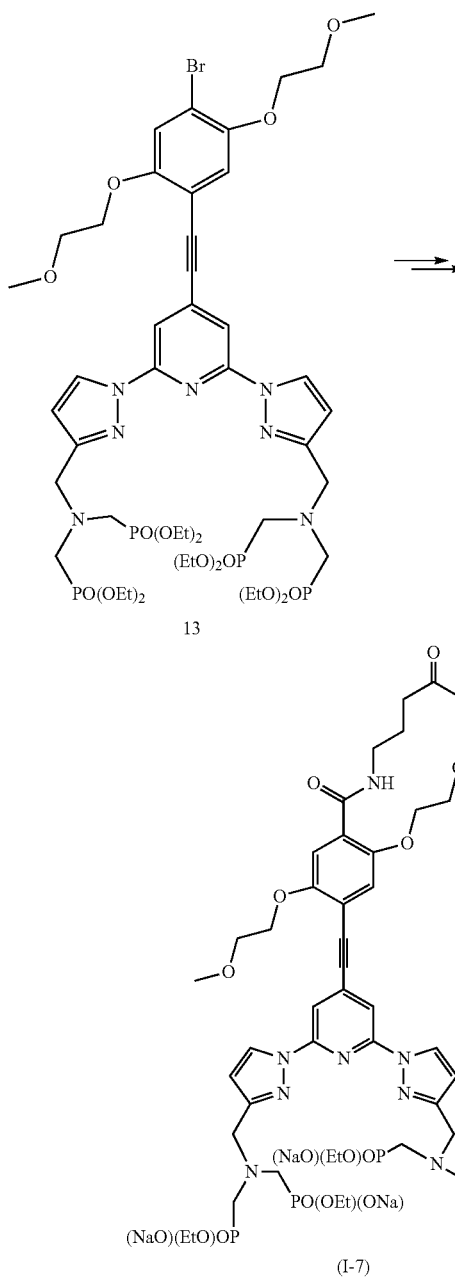

13

(I-7)

To a solution of 100 mg (0.083 mmol) of compound 13 obtained above in the second step for preparing the compound of formula (I-4) in a mixture of 5 ml of toluene and 1 ml of triethylamine, were added 52 mg of 4-ethylaminobutyrate hydrochloride (0.308 mmol) and 10 mg of Pd(PPh$_3$)$_2$Cl$_2$ (0.014 mmol). The resulting solution was heated at 70° C. for 12 hours under a continuous stream of CO. At the end of the reaction, the solvent was evaporated off and the residue was treated with water and extracted with dry dichloromethane. The white solid was dried and dissolved in water (10 ml), and 20 ml of aqueous sodium hydroxide solution (1N) were added. The solution was stirred at room temperature for 12 hours. Slow addition of diethyl ether brought about precipitation of the desired compound (I-7). This precipitate was centrifuged at 3000 rpm and washed with ether. The resulting compound was recrystallized twice by diffusion of ether into a concentrated methanol solution. The expected compound of formula (I-7) was obtained in a yield of 52%.

$^1$H NMR (200 MHz, D$_2$O) δ (ppm): 8.65 (s, 2H); 7.64 (s, 2H); 6.86 (s, 2H); 6.79 (s, 1H); 6.80 (s, 1H); 4.25 (t, 4H); 4.15 (m, 4H); 3.86 (m, 4H); 3.52 (m, 8H); 3.32 (s, 6H); 2.43-2.86 (m, 4H); 3.75 (s, 4H); 3.35 (s, 2H); 3.23 (s, 2H); 1.42-1.64 (m, 3H); 1.14 (m, 12H).

$^{31}$P {$^1$H} NMR (D$_2$O, 161 MHz): δ 28.27 ppm.

MS-ESI (methanol+2% TfA) 1035.2 ([M$^+$], 100).

Elemental analysis for C$_{44}$H$_{61}$N$_8$Na$_5$O$_{19}$P$_4$, 2H$_2$O:

|  | C | H | N |
|---|---|---|---|
| Calculated | 41.26 | 5.11 | 8.75 |
| Found | 41.01 | 4.86 | 8.46 |

The invention claimed is:

1. A compound of formula (I) below:

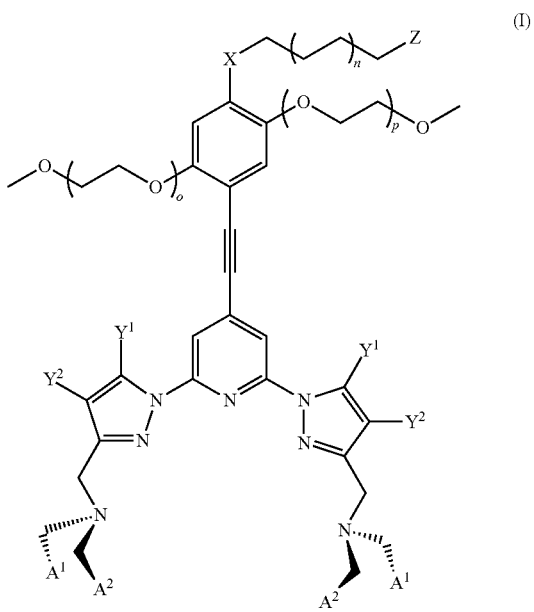

(I)

in which:
n, o and p, independently of each other, are integers ranging from 0 to 4;
A$^1$ represents a function —COOR$^1$ in which R$^1$ is a hydrogen atom or an alkali metal cation; or a group A$^2$;
A$^2$ represents a group —P(O)(OCH$_2$CH$_3$)(OR$^2$) or —P(O)(OR$^2$)$_2$ in which R$^2$ represents a hydrogen atom or an alkali metal cation;
each of the groups Y$^1$ and Y$^2$ represents a hydrogen atom or alternatively Y$^1$ and Y$^2$ together form a diradical forming one or more aromatic or heteroaromatic rings with the two carbon atoms that bear them, said aromatic rings optionally bearing one or more substituents chosen from a hydrogen atom, an amino group and a thiol group,
X represents a bond segment having a group selected from the group consisting of an amide function —C(O)—NH— and a triple bond —C≡C—;
Z is:
NH$_2$, a halogen, a phosphate,
a group COOR$^3$ in which R$^3$ is H, an alkali metal cation, a quaternary ammonium group N(R$^4$)$_4$$^+$ in which R$^4$ is H or a linear alkyl chain preferably containing from 1 to 4 carbon atoms, a succinimide group —N—(CO—CH$_2$—CH$_2$—CO)— or a pentafluorophenyl group —C$_6$F$_5$;

a biotin function (—CO—(CH$_2$)$_4$—C$_5$H$_7$N$_2$OS), a polyheteroaromatic group or a crown ether, an organic or mineral silyl cluster;

a macroscopic support.

2. The compound as claimed in claim 1, wherein R$^1$ and R$^2$ are chosen from K$^+$, Na$^+$ and Li$^+$.

3. The compound as claimed in claim 1, wherein the groups Y$^1$ and Y$^2$ form part of an aromatic or heteroaromatic ring.

4. The compound as claimed in claim 1, wherein the compound corresponds to one of the following formulae (I-1) to (I-8) below:

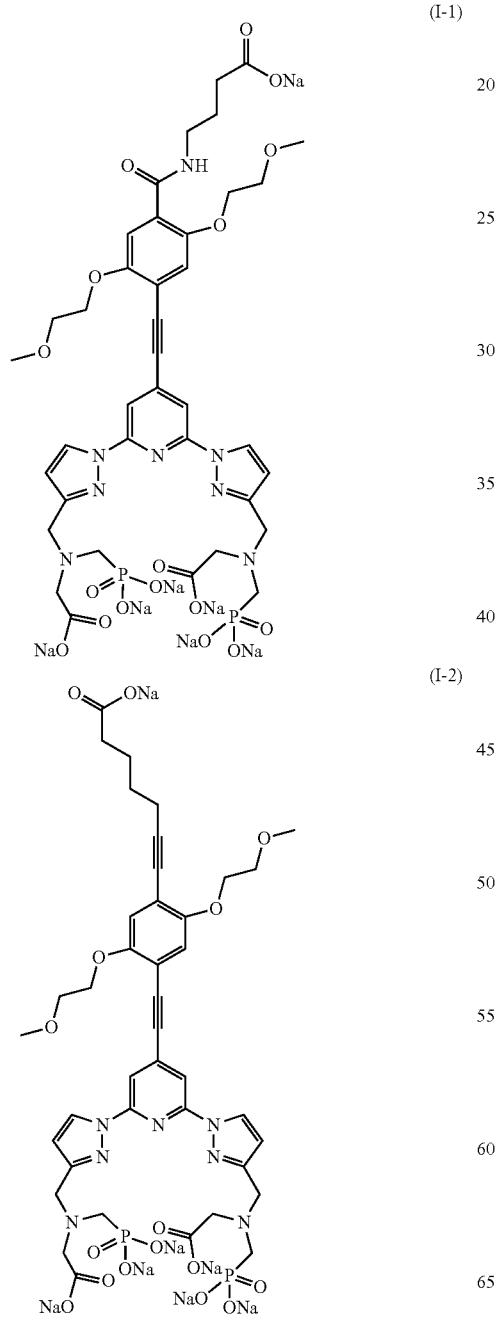

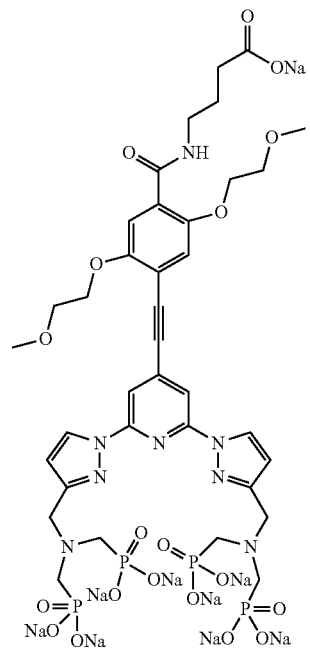

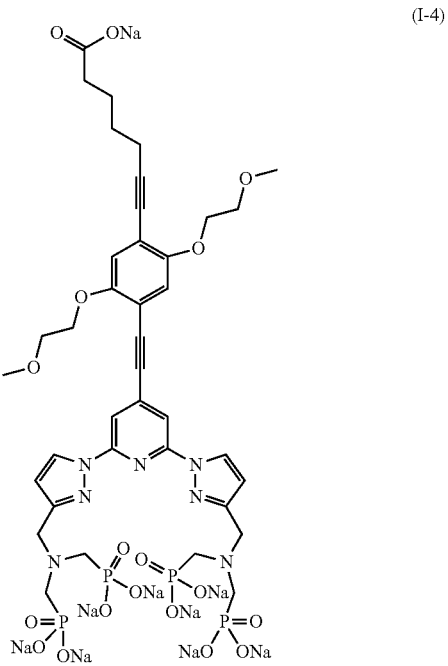

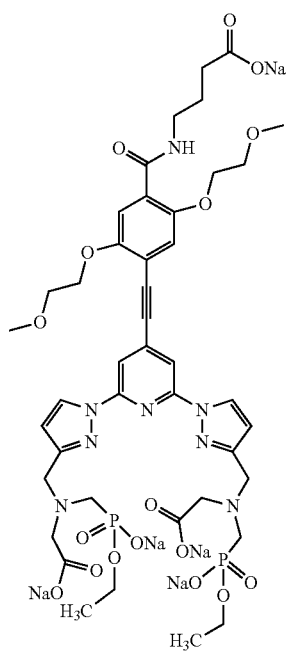
(I-5)
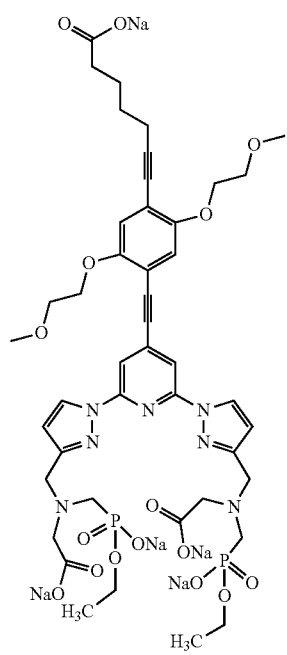
(I-6)
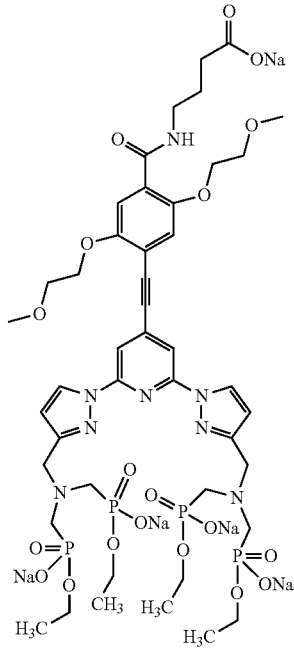
(I-7)
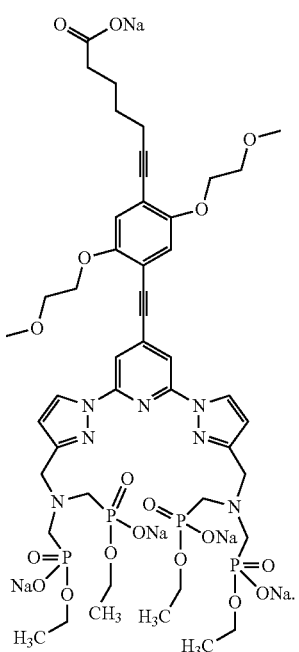
(I-8)
5. A process for preparing a compound of formula (I) as defined in claim 1, wherein said process comprises the following steps:
   1) a first step of nucleophilic substitution of the bromine atoms of a compound of formula (V) or (V') below:

(V)

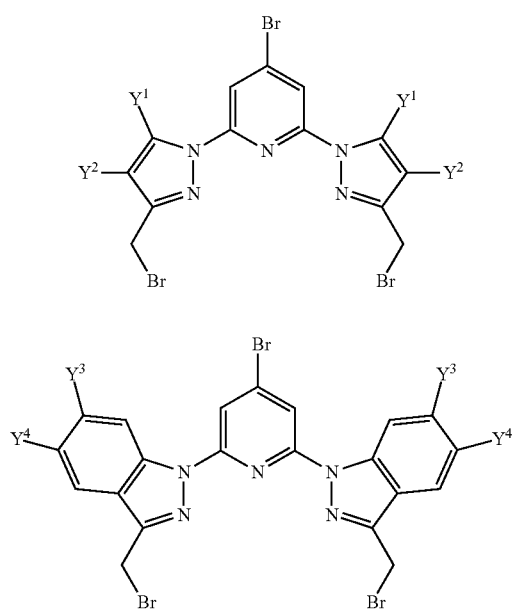

(VI)

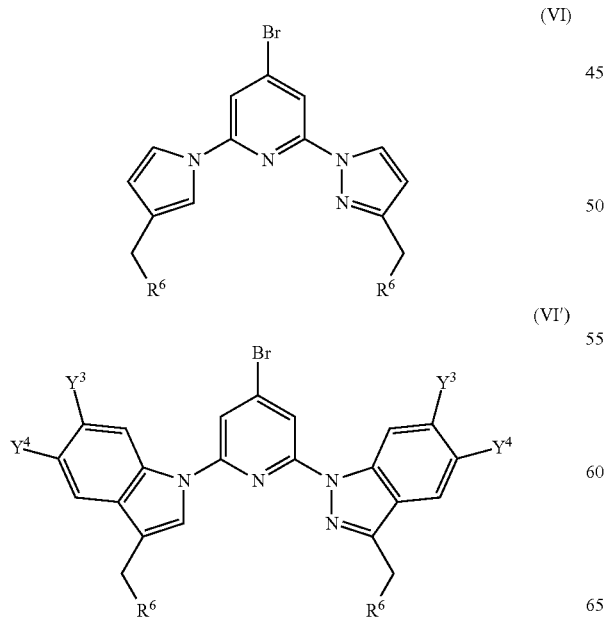

in which
the groups $Y^1$ and $Y^2$ have the same meaning as that indicated in claim 1 for the compounds of formula (I);
the groups $Y^3$ and $Y^4$, which may be identical or different, are selected from the group consisting of a hydrogen atom, an amino group and a thiol group;
said nucleophilic substitution being performed in an anhydrous solvent and at a temperature of between about 60° C. and 80° C., the presence of a mineral base and of a compound selected from the group consisting of the compounds of formula (III) below [NH(CH$_2$COOR$^{\prime 1}$)(CH$_2$P(O)(OR$^{\prime 2}$)$_2$] and the compounds of formula (IV) below [NH{CH$_2$P(O)(OR$^{\prime 2}$)$_2$}$_2$] in which R$^{\prime 1}$ and R$^{\prime 2}$, independently of each other, represent a linear or branched C$_1$-C$_4$ alkyl radical, to obtain a compound of formula (VI) or, respectively, of formula (VI'), below:

(VI)

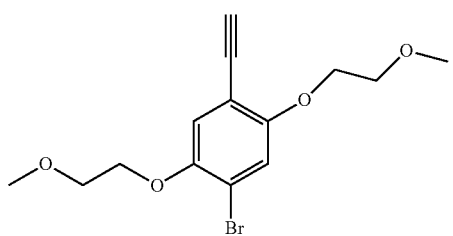

(VI')

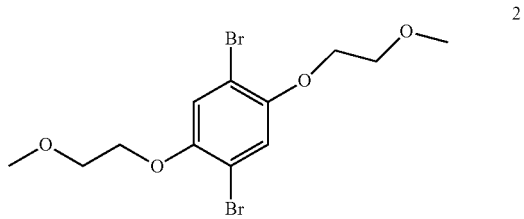

in which R$^6$ is chosen from the groups of formula R$^6$-a or R$^6$-b below:

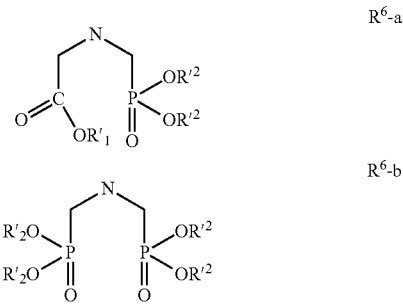

in which:
R$^{\prime 1}$ represents a linear or branched C$_1$-C$_4$ alkyl radical;
R$^{\prime 2}$ represents a C$_1$-C$_4$ radical;
ii) a second step of preparation of a compound 4 having the following formula:

4

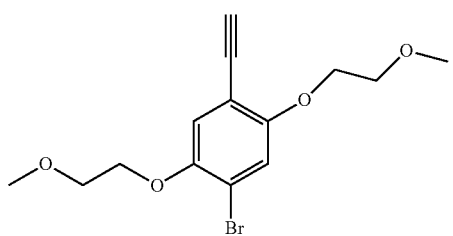

according to a process comprising the following substeps:
ii-a reaction of para-diphenol with 2-methoxyethanol tosylate, in an anhydrous solvent in the presence of a mineral base, at a temperature of about 80° C. for 12 hours approximately to obtain a compound 1 having the following formula:

1

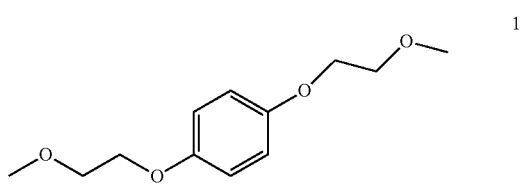

ii-b) a step of bromination of compound 1 obtained in the preceding step with bromine (Br$_2$), in a refluxing solvent for about 12 hours to obtain a compound having the following formula:

2

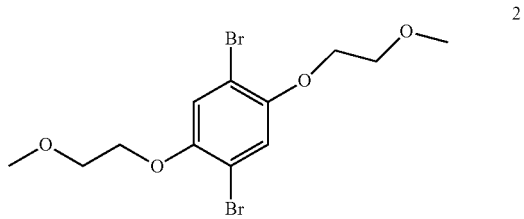

ii-c) a step of substitution of one of the two bromine atoms of compound 2 obtained in the preceding step, in a solvent, in the presence of diisopropylamine, a reagent (CH₃)₂C(OH)C≡CH, a palladium catalyst and CuI, to obtain a compound 3 having the following formula:

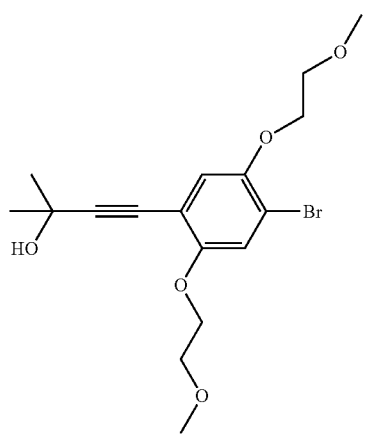

ii-d) a step of alkaline hydrolysis of compound 3 obtained above in the preceding step with an anhydrous strong base, in an organic solvent at a temperature of about 130° C. for 12 hours approximately, to obtain said compound 4;

iii) a third step of crossed coupling between compound 4 obtained above in step ii) and the compound of formula (VI) or, respectively, (VI'), obtained above in step i), in an organic solvent in the presence of a catalyst with palladium and triphenylphosphine, to obtain a compound of formula (VII) or, respectively, (VII'), below:

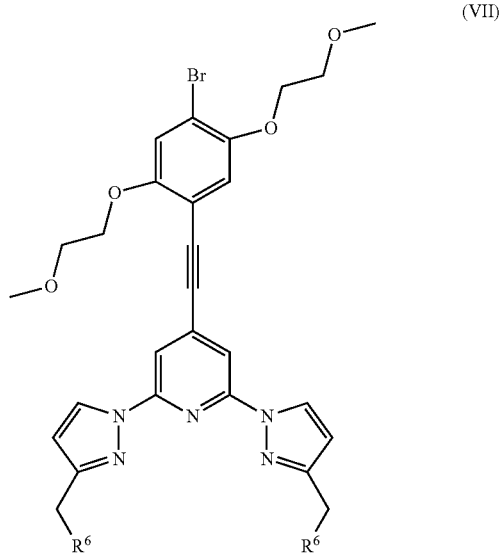

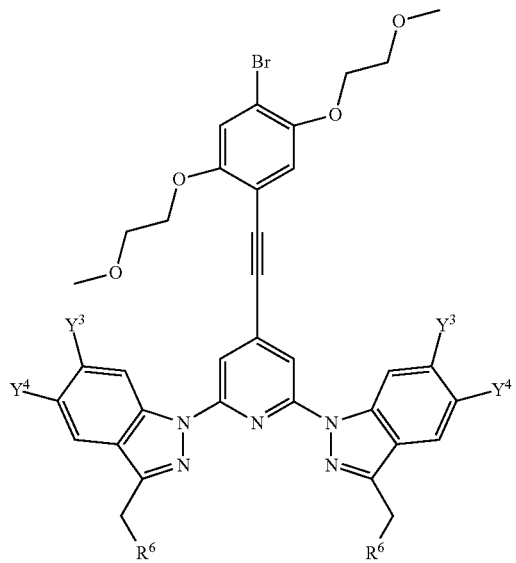

in which $R^6$ has the same meaning as in the compounds of formula (VI) or, respectively, (VI'), above;

iv) a fourth step in which the bromine of the compound of formula (VII) or, respectively, (VII'), is replaced with a group of formula $X-CH_2-(CH_2CH_2)_n-CH_2-Z$ in which n, X and Z have the same meaning as that indicated in claim 1 relating to the compounds of formula (I), by reaction with a suitable reagent, in the presence of an organometallic catalyst, in an organic solvent;

v) a fifth step in which the groups $R'^1$ and $R'^2$ are replaced, respectively, with groups $R^1$ and $R^2$, said groups being H or an alkali metal cation (for $R^1$) or an alkali metal cation (for $R^2$).

6. The process as claimed in claim 5, wherein, in the fifth step, the replacement of the groups $R'^1$ and $R'^2$ of the linear alkyl type with a cation $K^+$, $Na^+$ or $Li^+$ is perforated with KOH, NaOH or LiOH, respectively, in a polar solvent, at a temperature of between 20 and 100° C., or alternatively by using trimethylsilyl bromide in a solvent at room temperature followed by basic hydrolysis.

7. The process as claimed in claim 5, wherein in the fifth step, the replacement with H of groups $R'^1$ or $R'^2$ of the branched alkyl type is performed by reaction with trifluoroacetic acid in an aprotic organic solvent.

8. A complex of lanthanide or of a transition metal, wherein said complex comprises a lanthanide or transition metal ion complexed with a ligand of formula (I) as defined in claim 1.

9. The complex as claimed in claim 8, wherein the lanthanide ion is selected from the group consisting of the ions $Gd^{3+}$, $Lu^{3+}$, $Eu^{3+}$, $Th^{3+}$, $Dy^{3+}$, $Sm^{3+}$, $Er^{3+}$, $Yb^{3+}$, $Pr^{3+}$ and $Nd^{3+}$.

10. The complex as claimed in claim 8, wherein the transition metal ion is selected from the group consisting of the ions Cu(II), Co(II), Mn(II or IV), Ni(II), Fe(III), Pd(II) and Pt(II).

11. The complex as defined in claim 8, wherein said complex is a luminescent marker for two-photon absorption.

* * * * *